United States Patent
Tsujino et al.

(10) Patent No.: US 8,480,582 B2
(45) Date of Patent: Jul. 9, 2013

(54) IMAGE PROCESSING APPARATUS AND ULTRASONIC DIAGNOSIS APPARATUS

(75) Inventors: Hiroyuki Tsujino, Tochigi-Ken (JP); Masahide Nishiura, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 996 days.

(21) Appl. No.: 10/377,800

(22) Filed: Mar. 4, 2003

(65) Prior Publication Data
US 2003/0171668 A1 Sep. 11, 2003

(30) Foreign Application Priority Data
Mar. 5, 2002 (JP) .................. P2002-59160

(51) Int. Cl.
*A61B 8/00* (2006.01)
(52) U.S. Cl.
USPC .......................................... 600/437; 600/438
(58) Field of Classification Search
USPC ..................... 600/407, 437, 438; 382/128
See application file for complete search history.

(56) References Cited

U.S. PATENT DOCUMENTS

| 5,195,525 | A * | 3/1993 | Pelc ............................. 600/410 |
| 5,785,654 | A * | 7/1998 | Iinuma et al. .................. 600/441 |
| 5,800,356 | A * | 9/1998 | Criton et al. .................... 600/441 |
| 6,083,168 | A * | 7/2000 | Hossack et al. ................ 600/443 |
| 6,295,464 | B1 * | 9/2001 | Metaxas ......................... 600/407 |
| 6,491,636 | B2 * | 12/2002 | Chenal et al. ................. 600/450 |
| 6,728,394 | B1 * | 4/2004 | Chen et al. .................... 382/107 |
| 6,892,089 | B1 * | 5/2005 | Prince et al. .................. 600/410 |
| 7,356,172 | B2 * | 4/2008 | Fan et al. ....................... 382/128 |
| 2003/0083578 | A1 * | 5/2003 | Abe et al. ..................... 600/447 |
| 2003/0153823 | A1 * | 8/2003 | Geiser et al. .................. 600/407 |
| 2004/0087850 | A1 * | 5/2004 | Okerlund et al. ............. 600/407 |

FOREIGN PATENT DOCUMENTS

| JP | 7-184877 | 7/1995 |
| JP | 7-320068 | 12/1995 |
| JP | 8-84729 | 4/1996 |
| JP | 10-99334 | 4/1998 |
| JP | 10-151133 | 6/1998 |

OTHER PUBLICATIONS

U.S. Appl. No. 11/203,064, filed Aug. 15, 2005, Nishiura.
Official Action, issued Oct. 31, 2006, in Japan Patent Application No. 2002-058160 (with English translation.).

(Continued)

*Primary Examiner* — Jacqueline Cheng
(74) *Attorney, Agent, or Firm* — Oblon, Spivak, McClelland, Maier & Neustadt, L.L.P.

(57) ABSTRACT

An ultrasonic imaging apparatus and an ultrasonic diagnosis apparatus including the ultrasonic imaging apparatus comprise an image acquiring unit, extracting unit, tracking unit and physical parameter calculating unit. The image acquiring unit acquires image data of a subject, the extracting unit extracts a plurality of trackable characterizing points based on the acquired image data, the tracking unit tracks the movement of the characterizing points, and the physical parameter calculating unit acquires specific physical parameters, such as displacement, distortion and distortion velocity, based on the information derived from tracked results, of the characterizing points contained in each region of interest (ROI). Both of the ultrasonic imaging apparatus and an ultrasonic diagnosis apparatus make it possible to easily and accurately perform extraction of characterizing points and low-cost analysis of contraction/expansion functions of the heart or the like.

15 Claims, 17 Drawing Sheets

OTHER PUBLICATIONS

Masahide Nishiura, et al., "Active Contour Extraction Method Usnig Partial Shape Contraint Contour Model", Institute of Electronics, the Journal of Information and Communication Engineers, D-II vol. J83-D-II, No. 1, pp. 183-190, 2000.

Fai Yeung, et al., "Feature-Adaptive Motion Tracking of Ultrasound Imaage Sequences Using a Deformable Mesh", IEEE Transactions on Medial Imaging, vol. 17, No. 6 pp. 945-956, Dec. 1998.

* cited by examiner

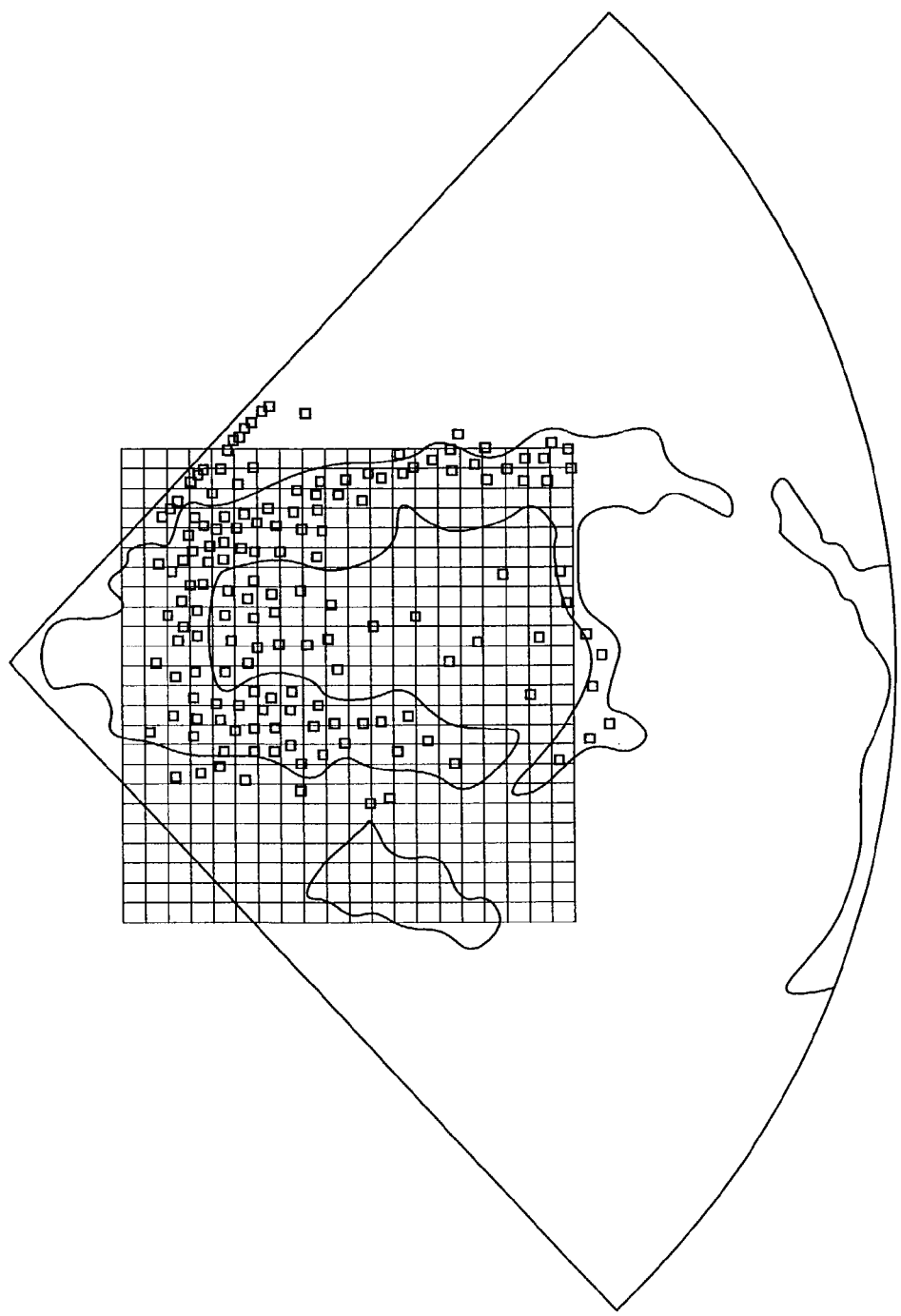

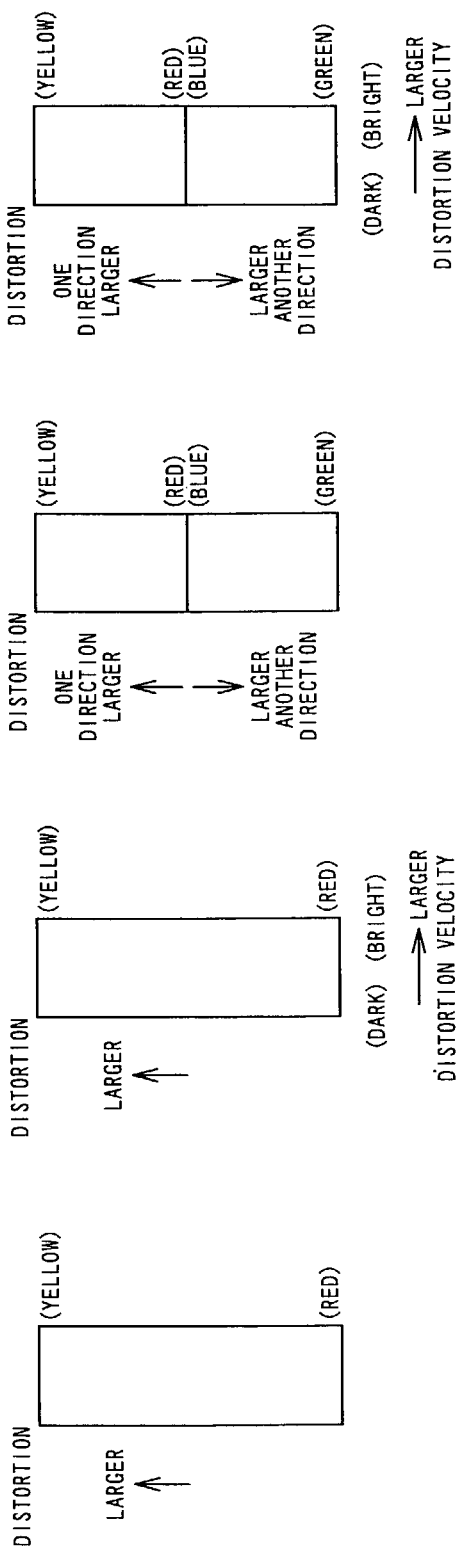

IMAGE PROCESSING APPARATUS AND ULTRASONIC DIAGNOSIS APPARATUS

BACKGROUND OF THE INVENTION

1. Field of the Invention

The present invention relates to an image processing apparatus and an ultrasonic diagnosis apparatus, and particularly to an ultrasonic diagnosis apparatus wherein the movements of characterizing points (tags) obtained from an image of an organism are tracked, and information with regard to various local functions of the tissue are estimated and output based upon the above-described tracking of the movements of tags, thereby enabling useful clinical information to be provided.

2. Description of the Related Art

Quantitative evaluation of local movement of the heart or the like (contraction/expansion functions) is a matter of great importance for understanding the function thereof. It is well known that, in the case of ischemic heart disease, for example, the change in regional wall movement occurs due to the shortage of blood supplied from coronary arteries.

Concerning quantitative evaluation methods for the regional wall movement, a great number of conventional methods have been proposed. Examples include "MRI tagging (magnetic marking) method" disclosed in Japanese Unexamined Patent Application Publication No. 7-184877, "two-dimensional movement vector detection by B-mode image", "tissue Doppler method", and the like.

The MRI tagging (magnetic marking) method is a method specific to MRI (magnetic resonance imaging), wherein magnetic marks (tags) from electromagnetic waves are placed onto an MRI image as a grid, and quantitative evaluation of the temporal change in the tags is performed, so that the movement or distortion of organic tissue is visualized. The MRI tagging method is a method wherein grid points, which are magnetic marks referred to as tags, are taken as sample points so as to detect movement and display a scene of distortion of the grid, and corresponds to an analytical method which is referred to the Lagrange method in physics (continuum mechanics). By use of the Lagrange method, temporal tracking the sample points enables contraction and expansion of cardiac muscle or the like to be directly calculated as a tensor property.

The "two-dimensional movement vector detection by B-mode image" includes conventional methods such as a method wherein movement vectors are estimated based upon the peak position of the two-dimensional cross-correlation coefficients, an optical flow method using the gradient of the image density, as a method for detecting the movement in the direction orthogonal to an ultrasonic beam. Information to be displayed includes movement vectors, tracks, cross-correlation value, and so forth.

The tissue Doppler method is a method wherein the movement of tissue is detected using the ultrasonic pulse Doppler or a color Doppler, and basically, only the component in the direction of the ultrasonic beam is detected. A method has been also proposed wherein two-dimensional movement components are obtained by making an assumption for the direction of the movement. The estimated and displayed information includes the difference of the velocities between two sample points, the distortion obtained by integrating the above difference, and so forth.

On the other hand, the twisting or distortion of cardiac muscle, which cannot be readily detected with conventional arrangements, can be analyzed using the MRI tagging method. However, there are problems that an MRI apparatus is an expensive apparatus, and also image acquisition using tagging cannot be performed in real time.

Accordingly, in general, the obtained MRI image is an image for a time period of a plurality of cardiac beats, and evaluation of the wall movement for each cardiac beat can not be made. In particular, it is well known that evaluation of the expansibility requires time-resolution with high precision, and consequently, sufficient analysis cannot be readily performed using the MRI due to the time-resolution of MRI (50 ms to 100 ms).

To the contrary, with the use of the two-dimensional movement vector detection by ultrasonic B-mode, while tracking can be performed on relatively large tissue with clear contours such as endocardium and annulus, or the like, or interference patterns due to random ultrasonic scatter, which are referred to as "speckle pattern", the trackable characterizing points cannot be readily specified.

Therefore, upon the two-dimensional movement vector detection by ultrasonic B-mode, temporal tracking arbitrary grid points within cardiac muscle cannot be performed as it can upon the tagging method in MRI.

If tracking is attempted with the use of the two-dimensional movement vector detection by ultrasonic B-mode, the temporal change (trail of movement, etc.) of only the trackable characterizing points can be displayed. Furthermore, while various types of improved methods have been proposed with regard to tracking algorithm itself, such as a method wherein compound processing is added to simple cross-correlation calculation, the precision of the methods is poor, and consequently the methods are hardly practiced in the clinical field. The characterizing points which are suitable to tracking must be selected in the event of performing tracking with high precision.

On the other hand, in the event of employing the tissue Doppler method, there is a problem that the apparatus is expensive due to necessity of having a cross-correlation computation circuit for Doppler calculation.

Moreover, the phase change (the change in a distance within the half-wavelength) detected by the tissue Doppler method is smaller than the movement amount of local myocardial portions (around 1 to 10 mm), and accordingly, the displacement of the myocardial portion is obtained by time integrating the detected instantaneous phase (velocity) in order to get the information with regard to the macroscopic movement of the cardiac muscle.

Therefore, accumulated error margin arisen by integrating the velocity information, leads to a problem the same as with performing the LaGrange analysis wherein a mark (tag) is placed onto a certain point, and direct tracking of the movement thereof is required. In particular, provided that time and spatial resolution is insufficient, interpolation processing for data is necessary in order to calculate movement amount, and the precision thereof also influences the final measurement precision.

Besides, with conventional arrangements, in either method described above, tracking of arbitrary positions within cardiac muscle cannot be performed, but specifying the initial position or region to be tracked must be made by manual operations, which is troublesome. That is, provided that a pointer or the like is placed onto a certain point, the point can be tracked. However, in the event of placing the pointer onto a point at which there are no structures, tracking of the point cannot be made. Consequently, a user must change the point on which the pointer has been placed, and procedures for selecting a trackable point one by one point by manual operations are troublesome for users.

Moreover, with regard to analysis methods, there is the problem of angular dependence. For example, whether the movement is expansion or contraction might depend on the direction parallel or orthogonal to the fiber of the same portion of cardiac muscle, and accordingly, different results are obtained depending upon the analysis direction and an incorrect diagnosis might be made. In other words, with the tissue Doppler method, basically tissue is one-dimensionally analyzed, i.e., the moving velocity of tissue in the beam direction is measured, so one-dimensional information is obtained, and consequently, the movement in other directions must be assumed (estimated) from projection components in the orthogonal direction. Moreover, tracking cannot be readily made in the other directions.

SUMMARY OF THE INVENTION

The present invention has been made taking the above-described problems into consideration, and it is an object of the present invention to provide an image processing apparatus and an ultrasonic diagnosis apparatus for easily and accurately performing extraction of characterizing points and low-cost analysis of contraction/expansion functions of the heart or the like without requiring specifying of the initial position or region to be tracked by manual operations.

In order to achieve the object, as one aspect of the invention, there is provided an image processing apparatus comprising: image acquiring unit for acquiring image data of subject; first tracking unit for tracking a plurality of points in the image based on at least one data of brightness and amplitude of the image data; and physical parameter calculating unit for calculating a specific physical parameter with regard to a change in a relative positional relationship among the plurality of position.

Preferably, the extracting unit is configured to extract the plurality of trackable characterizing points based on the acquired image data and the second tracking unit is configured to track the movement of the characterizing points.

It is preferred that the image processing apparatus has a region-of-interest (ROI) setting unit for setting a plurality of regions of interest onto the image displayed based on the image data, wherein the physical parameter calculating unit is configured to acquire the physical parameter based on the information from the plurality of the characterizing points contained in each of the regions of interest.

It is further preferred that the region-of-interest setting unit is configured to extract a contour of at least one of a heart and a myocardial region thereof and to set the regions of interest on an image based on the extracted result. For example, the region-of-interest setting unit may be further configured to classify the heart or the myocardial region thereof into a plurality of segments, and to set the regions of interest on the image based on the classification. In this case, a plurality of segments may be three segments of a base, a middle and an apex portion from an annulus to the apex of each side.

Further preferably, the extracting unit is configured to extract the characterizing points only within the bounds of the regions of interest and the tracking unit is configured to track the same.

Still preferably, the region-of-interest setting unit is configured to move at least one of the regions of interest based on information about movement of the plurality of characterizing points residing within the bounds of the regions of interest or of the plurality of characterizing points spatially neighboring each other.

It is also preferred that the image processing apparatus further comprises extracting unit for extracting the plurality of trackable characterizing points based on the acquired image data, region-of-interest setting unit for setting the plurality of regions of interest having an equally-spaced pattern on the image displayed based on the image data, correlating unit for correlating the extracted characterizing points to the regions of interest with equal shape, and deforming unit for deforming the regions of interest having an equally-spaced pattern based on the tracking result, wherein the physical parameter calculating unit is configured to calculate physical parameter with regard to the deformation of the region of interest. For example, the region-of-interest setting unit may be configured to set the regions of interest in an equally-spaced grid pattern and to automatically adjust a grid pitch of the equally spaced grid pattern.

Preferably, the physical parameter calculating unit is configured to acquire a deformation tensor from the information about deformation of the regions of interest and to separate the deformation tensor into a symmetric tensor and an asymmetric tensor. Or the main axis of the physical parameters is oriented to a direction orthogonal or tangential to one of the extracted endocardium face and epicardium face. It is also preferred that the physical parameter is one of the displacement, distortion and distortion velocity derived from deformation of the regions of interest set in a grid pattern. Still preferably, the extracting unit is configured to extract the characterizing points by detecting corner points from the image.

As another aspect of the invention, there is provided an image processing apparatus comprising: image acquiring unit for acquiring image data of a subject; tracking unit for tracking movement of a predetermined points involved in the image; region-of-interest setting unit for setting region of interest and altering the plurality of regions of interest sequentially; and physical parameter calculating unit for acquiring physical parameter based on the movement information of the regions of interest.

Preferably, the region-of-interest setting unit includes correcting means for correcting positional information of the regions of interest based on the statistical distribution of the plurality of characterizing points within the bound of the region of interest.

It is preferred that the image processing apparatus further comprising at least one of unit for displaying in colors the image data obtained by the physical parameter calculating unit and unit for displaying pieces of information formed by mutually combining the plurality of types of data obtained by the physical parameter calculating means. It is also preferably, the image data is a three-dimensional image data.

As described above, with the present invention, a plurality of temporally trackable characterizing points (portions which can be readily tracked) can be easily extracted from all the points on an ultrasonic image at the same time. Accordingly, there is no need for several points to be manually operated and confirmed as with conventional arrangements, but rather, a plurality of trackable points can be extracted for the region of the entire tissue at the same time, thereby reducing the burden placed onto the user.

Furthermore, with the characterizing points contained within the specified arbitrary region of interest, tracking can be easily and accurately made. Physical parameters can be obtained with high time-resolution and low-cost, as compared with MRIs. Similarly, the physical parameters can be obtained with low-cost and good precision without requiring a large-scale circuit, integration processing, or the like, as compared with Doppler methods. At this time, tracking is performed for only the characterizing points within the region of interest, and various physical parameters are calculated, thereby reducing time period for calculation.

In particular, with the heart region, information (regarding contraction, expansion, etc.) in the specific direction according to the shape of the heart can be analyzed in a two-dimensional or three-dimensional manner, thereby enabling the cardiac performance to be easily and objectively evaluated with good precision.

Moreover, amount movement of an arbitrary portion (e.g., grid point) is estimated from the tracking results of the plurality of characterizing points, thereby improving the precision.

Furthermore, a plurality of regions of interest are specified, and the distances between the regions of interest or the like are tracked, and thus quantitative information with regard to the macroscopic structure, which is useful for observing the change in the parameters of the macroscopic structure such as the valve, papillary muscle, apex cordis, or the like, thereby enabling the characteristic change in the shape of the heart due to myocardial infarction or the like to be measured with good precision.

BRIEF DESCRIPTION OF THE DRAWINGS

FIG. 4(b) is its simplified diagram substitutive for FIG. 4(a);

FIGS. 6(a) and 6(b) are explanatory diagrams describing an example of the movement of the region of interest with the ultrasonic diagnosis apparatus of the present invention, in which FIG. 6(a) depicts a shape of the region of interest when it is set, and FIG. 6(b) depicts a shape of the region of interest after it is altered;

FIGS. 9(a) and 9(b) are explanatory diagrams illustrating an example of displaying with color-coding in which FIG. 9(a) depicts tomographic image indicating the configuration of tissue is illustrated, and FIG. 9(b) depicts a distortion of a cardiac muscle overlaid on the tomographic image.

FIGS. 10(a) through 10(d) illustrate examples displaying color bars;

FIGS. 13(a) through 13(c) are explanatory diagrams describing the movement of a plurality of regions of interest, in which FIG. 13(a) depicts a plurality of regions of interest when they are set, FIG. 13(b) depicts a plurality of regions of interest in the event of contraction and FIG. 13(c) depicts a plurality of regions of interest in the event of expansion respectively.

DESCRIPTION OF THE PREFERRED EMBODIMENTS

Preferable embodiments according to the present invention will be specifically described with reference to the drawings below.

(First Embodiment)

A first embodiment of the present invention will now be described. The present embodiment has the advantage that characterizing points can be easily selected by automatically extracting and displaying a great number of trackable characterizing points on an ultrasonic image at the same time.

Besides, precision of estimation is improved by using a plurality of characterizing points, i.e., by estimating the movement amount of an arbitrary point (grid point) from the representative value of the movement amount of a plurality of tracking points for which tracking has been performed. In addition, a system is configured with an ultrasonic diagnosis apparatus with a low cost and high time-resolution, wherein the characterizing points are correlated with the grid points, so that calculation for distortion or the like can be easily performed, intuitive recognition can be made, and information regarding cardiac performance can be obtained by tagging.

Figure 1:
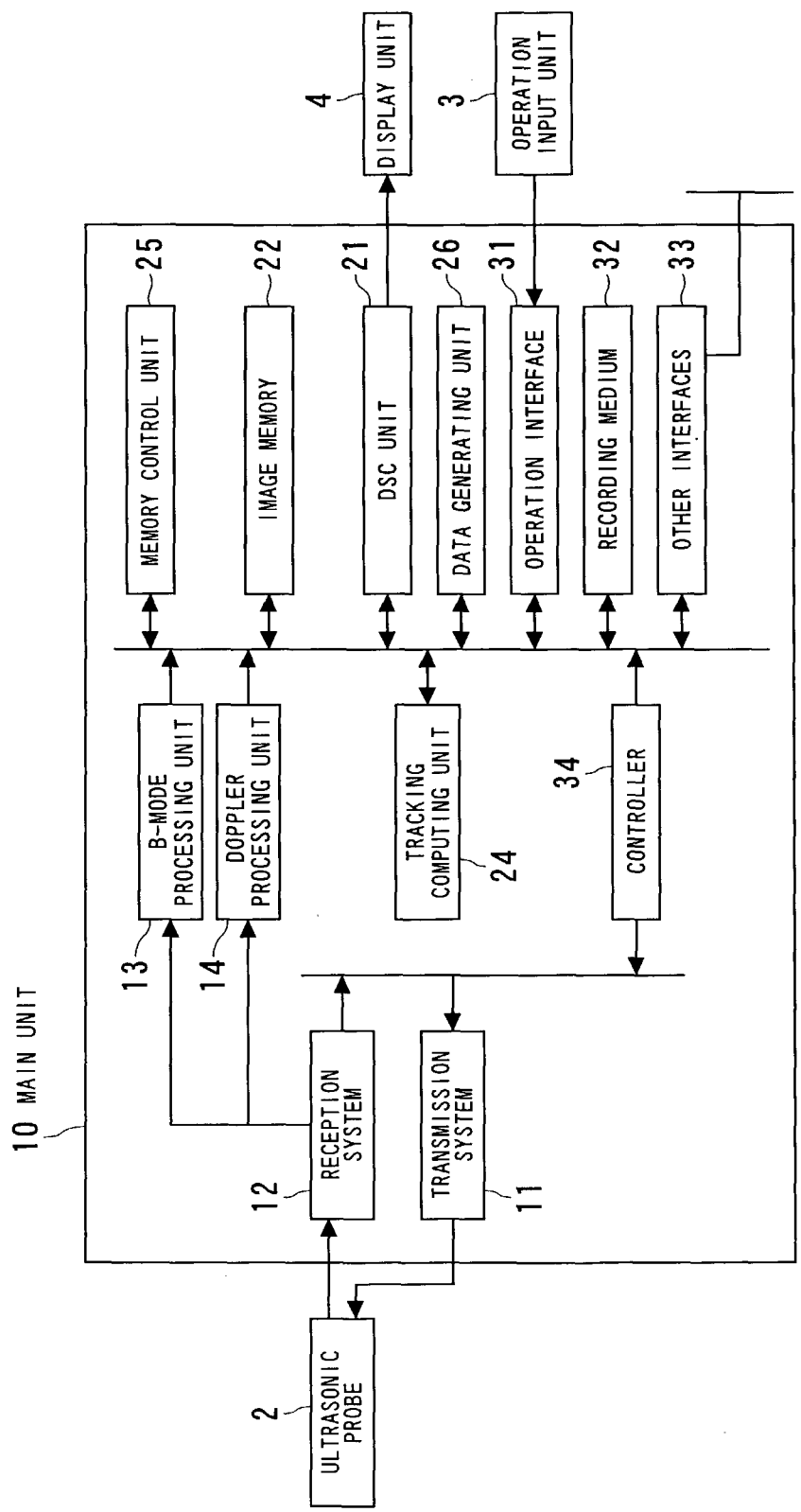
FIG. 1 is a block diagram illustrating an example configuration of an ultrasonic diagnosis apparatus according to a first embodiment of the present invention.

Preceding description of the features, an overall schematic configuration of hardware of an ultrasonic diagnosis apparatus to which the present invention is applied will be described with reference to FIG. 1. FIG. 1 is a block diagram illustrating an example configuration of an ultrasonic diagnosis apparatus according to the present embodiment.

An ultrasonic diagnosis apparatus has a hardware configuration including an ultrasonic probe 2 for performing transmission and reception of ultrasonic signals to and from the subject, a main unit 10 for driving the ultrasonic probe 2, and processing received signals from the ultrasonic probe 2, an operation input unit 3 which is connected to the main unit 10 whereby the user can input instruction information, and a display unit 4 for displaying an image, a region of interest (ROI), extracted characterizing points, results of tracking, and the like, as shown in FIG. 1.

The ultrasonic probe 2, while converting a pulse driving voltage obtained from the main unit 10 into ultrasonic pulse signals so as to being transmitted in the desired direction within a scan area in the subject, converts ultrasonic echo signals reflected from the subject into voltage echo signals of the ultrasonic echo signals corresponding thereto.

The operation input unit 3 includes a mouse, button, keyboard, trackball, or the like, with which the user can specify a region of interest (ROI) or a time phase of interest. These operation devices are used for the user inputting required transmission/reception conditions, selection information regarding the state of display, or the like, as well as specifying patient information, device conditions, region of interest (ROI), time phase of interest, whether or not to start tracking, or the like.

The main unit 10 comprises a controller 34 serving as a control center of the entire apparatus, a transmission system 11 and reception system 12, connected to the ultrasonic probe 2, a B-mode processing unit 13 for obtaining B-mode tomography image of the subject, a Doppler processing unit 14, a DSC (digital scan converter) unit 21 disposed on the output side, image memory 22, a tracking computing unit 24 for tracking extracted characterizing points, a memory control unit 25 for performing processing such as image synthesizing for graphic data, such as characterizing points or a region of interest in a grid pattern with regard to image information stored in the image memory 22, a data generating unit 26,which has a color coding circuit or the like, for generating graphic data such as the display state (color, shape, or the like) of the characterizing points or the region of interest in a grid pattern, corresponding to instructions from the controller 34, an operation interface 31, a recording medium 32 for recording various types of programs such as apparatus control programs, computation programs for extracting the characterizing points (which is a principal unit in the present invention), programs for calculating physical parameters, and the like, and other interfaces 33. The controller 34 also receives operation signals from the operation input unit 3 via the operation interface 31. These components may be configured with hardware such as integrated circuits, or also may be configured with modular software programs.

The transmission system 11 is made up of transmission circuits such as a delay circuit and a pulse circuit, which are omitted from the drawings, and the reception system 12 comprises reception circuits such as an A/D converter and an adder. Pulsed ultrasonic waves are generated and transmitted to transducers of the probe 2, and echo signals scattered in tissue of the subject are received by the same probe 2, thereby obtaining received signals.

The output from the reception system 12 is transmitted to the B-mode processing unit 13. The echo signals are subjected to various types of filtering processing, logarithm amplification, envelope detection processing, or the like, thereby generating data wherein the signal intensity is indicated with the luminance. The Doppler processing unit 14 performs frequency analysis for velocity information from echo signals, and transmits the analysis results to the DSC unit 21.

The DSC unit 21 converts a train along each raster scanned by ultrasonic scanning to a train along each raster in a general video format such as a TV format. The image memory 22 and the memory control unit 25 perform image synthesizing for character information and a scale regarding various types of setting parameters generated by the data generating unit 26, graphic data indicating the region of interest, and, if performance of tracking is required, various graphic data indicating the characterizing points automatically extracted and data such as charts indicating the calculation results of physical parameters calculated based upon the tracking results. The synthesized image is output to display unit 4, thus, tomographic images indicating the figuration of tissue of the subject are displayed on the display unit 4.

The user can also read out the image data stored in the image memory 22, for example, following the diagnosis, for example.

The controller 34 has the functions of a information processing device (computer) including a CPU and memory, and serves as control means for controlling actions of the present ultrasonic diagnosis apparatus proper following precedently programmed procedures.

The controlled actions include processing for the display state of a diagnosis mode, transmission/reception conditions, region of interest, and so forth, which has been instructed by the user via the operation input unit 3, and further includes transmission control (transmission timing, delay of transmission, and the like) to the transmission system 11, reception control (delay of reception and the like) to the reception system 12, instructions for generating display data to the data generating unit 26, instructions for performing tracking processing for the tracking computation unit 24 by reading and executing programs and data necessary for extraction of characterizing points and tracking according to the present invention or the like, which are recorded in the recording medium 32, instructions to execute programs or the like, for calculating physical parameters regarding distortion or the like based upon the tracking results, and processing for controlling software modules in a centralized manner.

The recording medium 32 performs storage of the diagnosis images described above, and also stores various types of programs such as various characterizing-point-extraction software programs and physical-parameter-calculation programs.

Moreover, the controller 34 reads out output signals directly from the reception system 12, or image luminance signals via the B-mode processing unit 13, performs characterizing points extracting processing, tracking processing, physical parameters calculation processing, or the like according to the present invention, and displays the results on the display unit 4 via the DSC unit 21. The results are alternatively stored in the recording medium 32 as image files, or transmitted to an external information processing device (PC), printer, external recording medium, diagnosis data base, electronic clinical record system, or the like.

General description will be made regarding actions with the ultrasonic diagnosis apparatus 1 having the hardware configuration described above.

Provided that B-mode diagnosis is commanded, echo signals received by the reception system 12 via the ultrasonic probe 2 are converted into video signals by the B-mode processing unit 13, and is input to the DSC unit 21 as image data. The image data transmitted to the DSC unit 21 is scan-converted into B-mode image data in a video format following being subjected to post-processing such as smoothing. The B-mode image data is further transmitted to the display unit 4 in real time. At this time, the B-mode image is displayed on the display unit 4 with necessary graphic data being superimposed thereon.

On the other hand, a plurality of frames for example of at least one of image data with regard to ultrasonic scanning prior to scan-conversion generated during scanning, and the image data in a video format following scan-conversion, are stored in the image memory 22 by the DSC unit 21.

The user can read out the image data stored in the image memory 22 and use the image data again following scanning (i.e., after diagnosis in real time), and a plurality. of frames of image data read out can be played back in an animated manner.

At this time, the frame rate of the image read out from the image memory 22 can be altered, thereby enabling slow-motion playback, playback in a frame-by-frame mode, and freeze-frame. The playback is generally performed in an endless mode. For example, following displaying the tenth heart beat image, the playback loops back to the first heart beat image again.

The user sets "time phase of interest (time period range of interest)" for measurement with time phase-of-interest setting means set up in the operation input unit 3. Thus, an arbitrary area of the image memory 22 is predetermined as an area for time phase of interest. Upon the user commanding beginning of playback following setting the time phase of interest, only the images in the range of the time phase of interest are played back in endless mode. For example, in the event of setting the time phase of interest to a contraction period, display is performed with regard to only the contraction period.

Following setting the time phase of interest as described above, the user sets the region of interest (ROI) for characterizing point on the image in the range of the time phase of interest with the operation input unit 3. The region of interest (ROI) for characterizing point extraction is superimposed on an image of the organism under control of the memory control unit 25 and the DSC unit 21.

Here, upon the user beginning the mode for automatically displaying trackable characterizing points, characterizing point extraction processing is performed by executing the characterizing point extraction programs based upon image data stored in the image memory 22, and the characterizing points for the region of interest with regard to the time phase of interest are displayed. The tracking computation unit 24 performs temporal tracking computation based upon the above characterizing points, and the physical-parameter-calculation program calculates various physical parameters such as distortion, based upon the tracking computation results. The computation results are displayed on the display unit 4.

According to the present embodiment, image information is temporarily stored in the image memory 22, and characterizing points extracted on the image can be displayed in a superimposed manner. Furthermore, temporal tracking is performed for required characterizing points, and calculation for physical parameters such as distortion is performed based upon the tracking results. Here, the physical parameters include distortion of tissue, distance, velocity, acceleration, and so forth.

The data generating unit 26 generates graphic data such as charts, indicating characterizing points, the region of interest, or physical parameters calculation results corresponding to the instructions from the controller 34, and the image data in the image memory 22 is subjected to various processing such as image synthesizing, by the memory control unit 25.

As described above, the memory control unit 25 receives image data of the transmitted B-mode images, and further receives graphic data, serving as a supplement to the image, and charts and/or values indicating the calculation results, and synthesizes the image and the supplementary data in a suitable manner such as a superimposed manner and arranged manner, based upon instructions from the controller 34.

The final data synthesized as described above is transmitted to the display unit 4. The display unit 4 displays images containing tissue images of the subject and extracted characterizing points. Required portions and/or data with the image is subjected to computer color-enhancing as appropriate.

Further detailed software configuration for characterizing point extraction and so on configured as above described, will be described below.
(Software Module Configuration)

The present embodiment has a software configuration which will be described below, for easily and accurately performing tracking with regard to characterizing points contained in a predetermined arbitrary region of interest.

In the present embodiment, detailed description will be made with regard to a case wherein a region of interest in a grid pattern is determined, and tracking is performed for a number of characterizing points contained therein, so that physical parameters in the relatively local region (e.g., around 5 mm) are computed and displayed.

Figure 2:
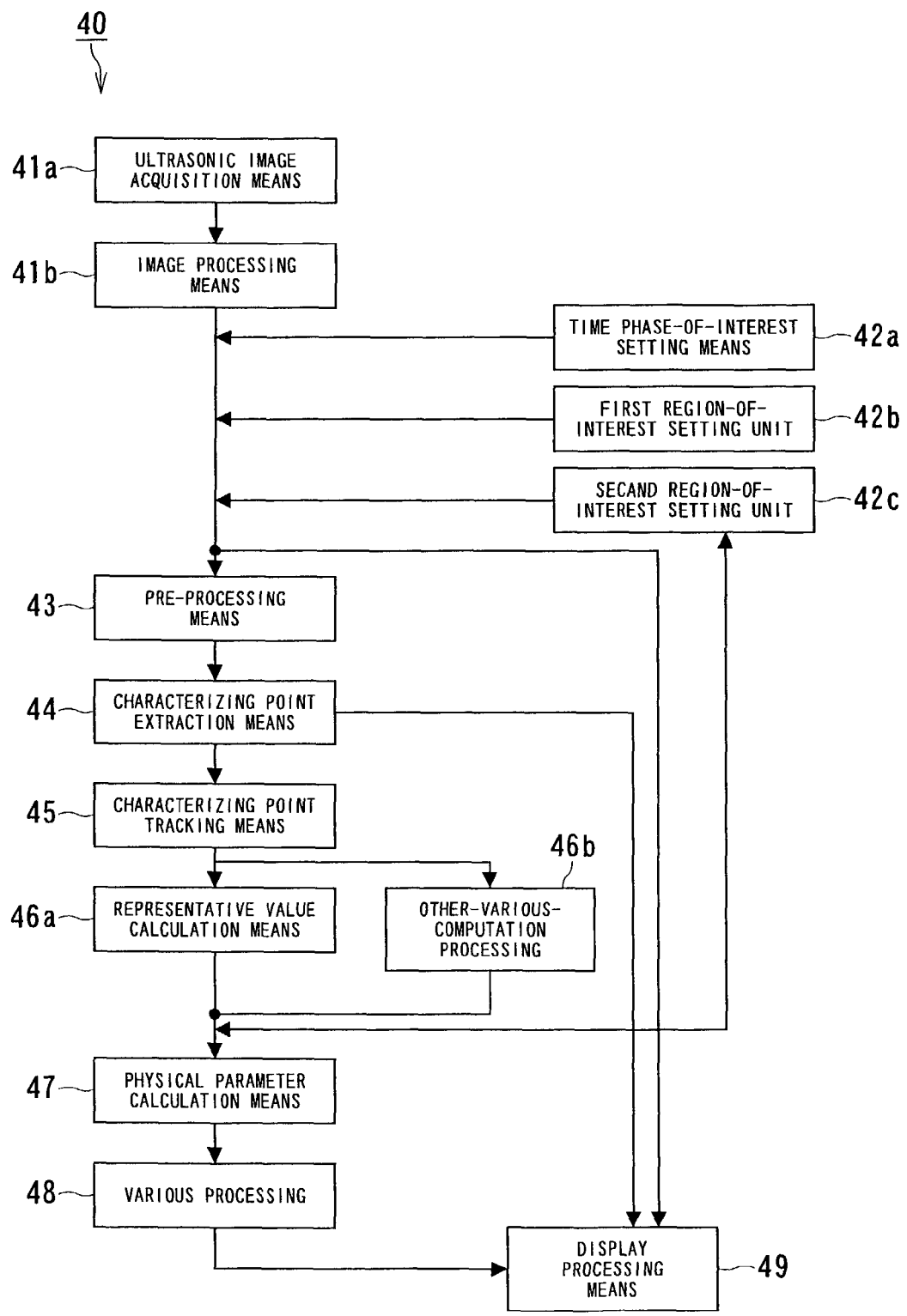
FIG. 2 is a functional block diagram illustrating an example software module configuration of the ultrasonic diagnosis apparatus shown in FIG. 1.

In the ultrasonic diagnosis apparatus according to the present embodiment, a software module configuration 40 comprises ultrasonic image acquisition means 41*a*, time phase-of-interest setting means 42*a*, a first region-of-interest setting unit 42*b*, a second region-of-interest setting unit 42*c*, image processing means 41*b*, pre-processing means 43, characterizing point extraction means 44, characterizing points tracking means 45, representative point calculation means 46*a*, other-various-computation processing 46*b*, physical parameter calculation means 47, various processing 48, and display processing means 49, as shown in FIG. 2.

Note that the characterizing point extraction means in the present embodiment corresponds to the extracting means in the present invention. Similarly, the characterizing points tracking means in the present embodiment is corresponding to the tracking means in the present invention. Furthermore, the first region-of-interest setting unit and the second region-of-interest setting unit in the present embodiment make up the region-of-interest setting means in the present invention. Moreover, the second region-of-interest setting unit includes the correcting means in the present invention. That is, in the present embodiment, the region-of-interest setting means includes the correcting means.

The ultrasonic image (B-mode) acquisition means 41*a* performs acquisition of ultrasonic B-mode images, and functions thereof will be described below in outline. That is, ultrasonic waves transmitted from the ultrasonic probe 2 are received by the same ultrasonic probe 2 as reflection signals from the organism. The echo signals subjected to phase addition by the reception circuit are subjected to logarithm amplification and envelope detection by a B-mode processing unit 13, the information regarding the amplitude thereof is output as the luminance information, which is reconstructed into an image by the DSC unit 21 so as to be displayed. While detailed description will now be made with regard to an ultrasonic diagnosis apparatus for obtaining normal two-dimensional tomographic images, the configuration can be extended to three-dimensional cardiac performance analysis by employing three-dimensional reconstruction means.

The time phase-of-interest setting means 42*a* has functions of setting time phase (range for analysis) for analysis with regard to animated images of the heart or the like, in motion. Concerning setting of the time phase of interest, a particular time range such as only the N-beat period, the contraction period or the expansion period, may be automatically extracted by an electrocardiogram, or, the user may manually set an arbitrary period. (In the case of stress echo test, a table for specifying the length of a contraction period based upon the cardiac rate is prepared.) Note that the range for analysis is preferably specified on the image which has been already stored on the image memory 22.

Figure 6A:
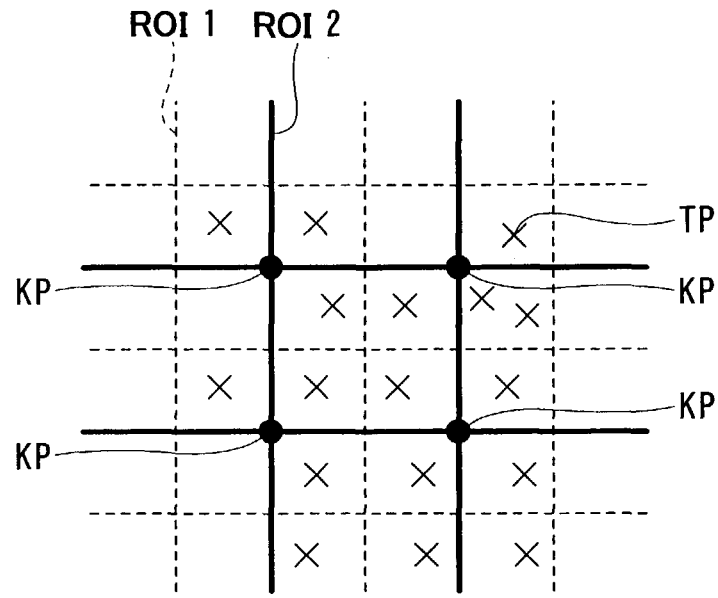
Figure 6B:
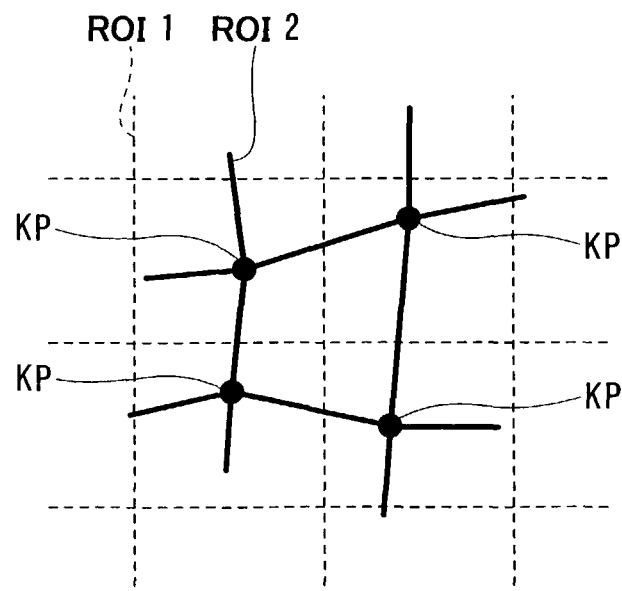

The first region-of-interest setting unit 42*b* sets a region of interest for tracking on an image data indicating the information with regard to the interior of the subject, and for example, sets a region of interest ROI1 for tracking, illustrated in a general grid pattern with dotted lines as shown in FIG. 6(*a*).

The second region-of-interest setting means 42*c* sets a region of interest ROI2, which is formed in a equally-spaced grid pattern displayed with solid lines as shown in FIG. 6(*a*), on image data indicating the information with regard to the interior of the subject. The second region-of-interest setting means 42*c* changes and moves the position of the region of interest ROI2 in such a manner that the grid points KPs are moved based upon the movement information regarding a plurality of characterizing points TPs within the region of interest ROI1 for tracking described above, or a plurality of characterizing points TPs spatially neighboring each other.

Accordingly, the shape of the region of interest ROI2 is altered corresponding to movement of a plurality of tracked characterizing points TPs within the region of interest ROI1 for tracking, and physical parameters (distortion amount, rotation amount, gap amount, and the like), which will be described later, can be calculated based upon the movement amount of the region of interest ROI2 in a grid pattern.

Figure 4A:
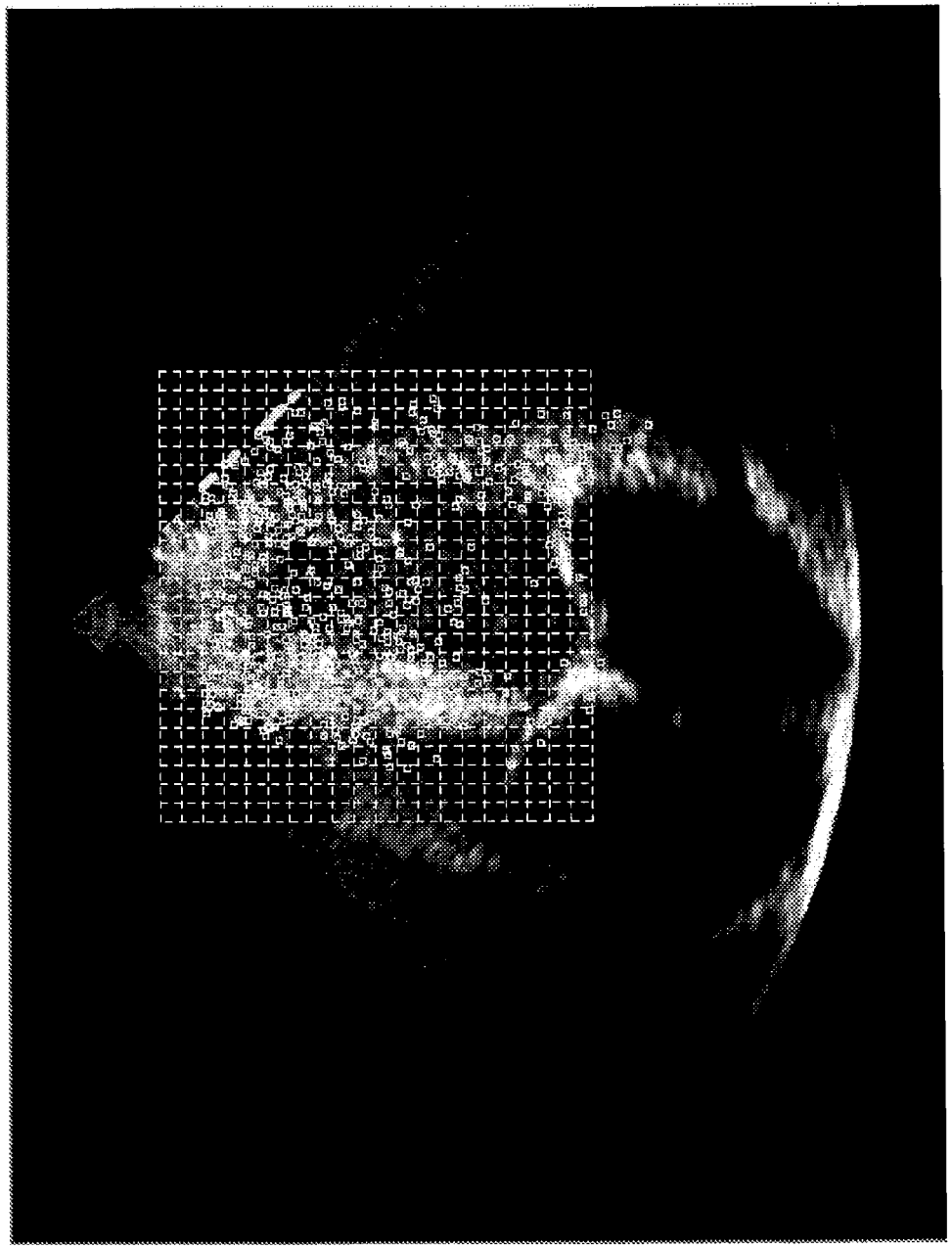
FIG. 4(a) is an explanatory diagram illustrating an example of a region of interest in a grid pattern which is set on an image with the ultrasonic diagnosis apparatus.

More specifically, a two-dimensional grid-patterned region of interest (ROI) is specified on a B-mode tissue image as shown in FIG. 4, for example. The user may manually set the present region of interest, or an arrangement may be made wherein a predetermined region of interest is superimposed on the B-mode image. The spacing of the grid pattern is preferably around several millimeters. As will be described later, the size of grid (spatial resolution) and the measurement precision (stability) are a trade-off, so the size of grid may be automatically determined according to the properties of the object for measurement.

Note that the region of interest in a grid pattern is preferably set for only an area corresponding to the cardiac muscle portion in the case of the heart, for example. Thus, restriction of the region of interest causes reduction of calculation time period for tracking computation for characterizing points as will be described later, and there is also the advantage that unnecessary results, such as the interior of the heart chamber, are not displayed.

Concerning a method for obtaining contours of the heart or cardiac muscle portions, automatic contour extraction processing, disclosed in Japanese Patent Application Publication (unexamined) No. 7-320068 for example, is preferably performed. The automatic contour extraction processing extracts endocardium using the statistical nature of images. It is further necessary to obtain the information regarding the epicardium side for extracting cardiac muscle. However, epicardium is generally obscure, so in many cases, extraction thereof cannot be readily performed. In this case, the epicardium side is set externally from the endocardium, which has been automatically extracted, by a predetermined distance, e.g., 15 millimeters or the like, and the region therebetween is determined as a myocardial region for simplification, thereby enabling the calculation region easily being restricted with relatively good precision.

Moreover, as another method for extracting myocardial portions, a method using region dividing with image luminance values may be employed. With regard to ultrasonic images, the myocardial portions are generally visualized with the luminance greater than the heart chamber portions, and accordingly, the myocardial portions can be extracted by extracting the regions with luminance greater than a suitably determined threshold.

The image processing means 41b performs image processing for the ultrasonic image which has been set by the time phase-of-interest setting means 42a so that the region of interest which has been set by the region-of-interest setting means 42b can be formed.

The pre-processing means 43 performs various types of pre-processing (e.g., processing for reduction of dynamic range, binary processing, or the like) prior to tracking processing by the characterizing point tracking means 45, thereby facilitating the following tracking to be performed, so as to improve precision. That is, while images in various states are expected to be acquired depending upon patients, reproducibility of tracking can be improved by performing various processing so as to facilitate post-processing tracking algorithm to be executed with good precision, for various types of input images.

For example, binary processing is performed for input images to facilitate tracking, so as not to obtain results that differ from one patient to another. The processing for narrowing the dynamic range has also the same effects. Moreover, an arrangement may be made wherein transmission/reception conditions such as setting of high-frequency transmission are controlled as well as the image processing, so as to set the optimal conditions such that the tracking algorithm is readily executed.

The characterizing point extraction means 44 extracts characterizing points (tags) which can be tracked. Note that, as for MRIs, trackable marks (tags) in a grid pattern are added on an image by applying high-frequency electromagnetic waves to an organism, and a scene of the squared grid being deformed over time can be observed. However, conventional ultrasonic devices have not been able to perform addition of such marks.

Characterizing points (ultrasonic tags) are defined as described below. is, The characterizing point is used for temporal tracking of the position, so it is necessary that the point can be tracked by executing predetermined algorithm as will be described later. According to the present embodiment, corner detection for detecting corner points or the like, for example, is employed as a method for extracting a structure.

A corner point can be defined as a point wherein the luminance thereof is markedly altered in the X direction and in the Y direction on the image, respectively. Accordingly, the direction of the movement can be determined by detecting corner points and employing the detected corner points as the characterizing points. There are various methods for corner detection, and a method using the determinant of the Hessian matrix represented by the following expression can be employed, for example.

$$H = \begin{vmatrix} Ixx & Ixy \\ Ixy & Iyy \end{vmatrix} \qquad \text{[Expression 1]}$$

Where Ixx and Iyy denote the second differential of luminance I(x,y) regarding the X direction and the Y direction, respectively, and Ixy denotes the second differential of luminance I(x,y) regarding the X direction and the Y direction.

In the case of ultrasonic images, the absolute value |H| of each point is calculated following smoothing for reducing the influence of noise, and the point with the maximal value thereof is detected as a corner point.

Regarding another method for corner detection, a SUSAN operator, for example, is preferably employed. As for a SUSAN operator, a mask area in a round shape is defined, and the number of pixels with luminance value near the luminance of the center point of the round-shaped mask is counted within the round-shaped mask area. The count value has a nature of being minimal when the center of the mask is situated at a corner point. Accordingly, the count value of the SUSAN operator is calculated at each point, and the point with the minimal count value is detected as a corner point.

As described above, while the Hessian determinant is applied to having change in luminance in the X direction and the Y direction, but is readily influenced by noise, the SUSAN operator can detect corner points without influence of noise, and accordingly is more preferable.

Besides corner detection, various methods for detecting characterizing points are also assumed, and either method can be used.

For an example of the most simple method for corner detection, a corner point can be defined as a point wherein the first differential of the point in the X direction and the Y direction of an image, i.e., the values, $\Delta x(i,j)=f(i,j)-f(i-1,j)$, $\Delta y(i,j)=f(i,j)-f(i, j-1)$ have values greater than a predetermined value, where $f(i,j)$ denotes a pixel value (luminance value) at the coordinates $(i,j)$ on a digital image.

Figure 3A:
FIG. 3(a) is an explanatory diagram illustrating an example of displaying trackable characterizing points extracted by the ultrasonic diagnosis apparatus on an image.
Figure 3:
FIG. 3(b) is its simplified diagram substitutive for FIG. 3(a)

Ordinarily, the spacing of the characterizing points defined by corner detection is not uniform as shown in FIG. 3. However, tracking results can be correlated with the grid points as will be described later. The characterizing point tracking means 45 temporally tracks characterizing points (tags) within the region of interest with regard to time. As a method for tracking characterizing points on a B-mode image (pattern matching), various methods can be employed starting with basic methods such as the cross-correlation method, density gradient method (optical flow method), or the like, for example. The extracted individual characterizing points can be tracked for each frame by the ordinary pattern matching method, but in general, precision is insufficient in tracking with one point only, and consequently stable measurement results cannot be readily obtained. For example, with conventional arrangements, tracking of a large structure such as contours of the heart and annulus, has been made, but it has been difficult to track a number of characterizing points within cardiac muscle.

However, the precision and stability of tracking can be improved by estimating movement amount of representative points in the region of interest from the tracking results of a plurality of characterizing points neighboring each other based upon the physical restriction that the neighboring cardiac muscle portions situated closely one to another perform the similar movement, for example, as will be described below.

The representative value calculation means 46a has functions of calculating a representative value of a plurality of characterizing points from the tracking results with regard to the plurality of characterizing points contained within a local region of interest (within a grid). In general, the detected characterizing points are distributed at irregular intervals as shown in FIG. 3, so the characterizing points cannot be readily correlated with the region of interest in a grid pattern described above. As the most simple method, tracking results with regard to one point which is the closest to the grid point can be output as the tracking results with regard to the grid point. However, it is preferable that the stability of tracking is improved by tracking a plurality of characterizing points and outputting the representative point thereof. For example, in the region with a predetermined grid pitch (e.g., 5 mm) containing a plurality of characterizing points (e.g., five points), the average of tracing results of each characterizing point is output as a representative value of the grid point.

Figure 5:
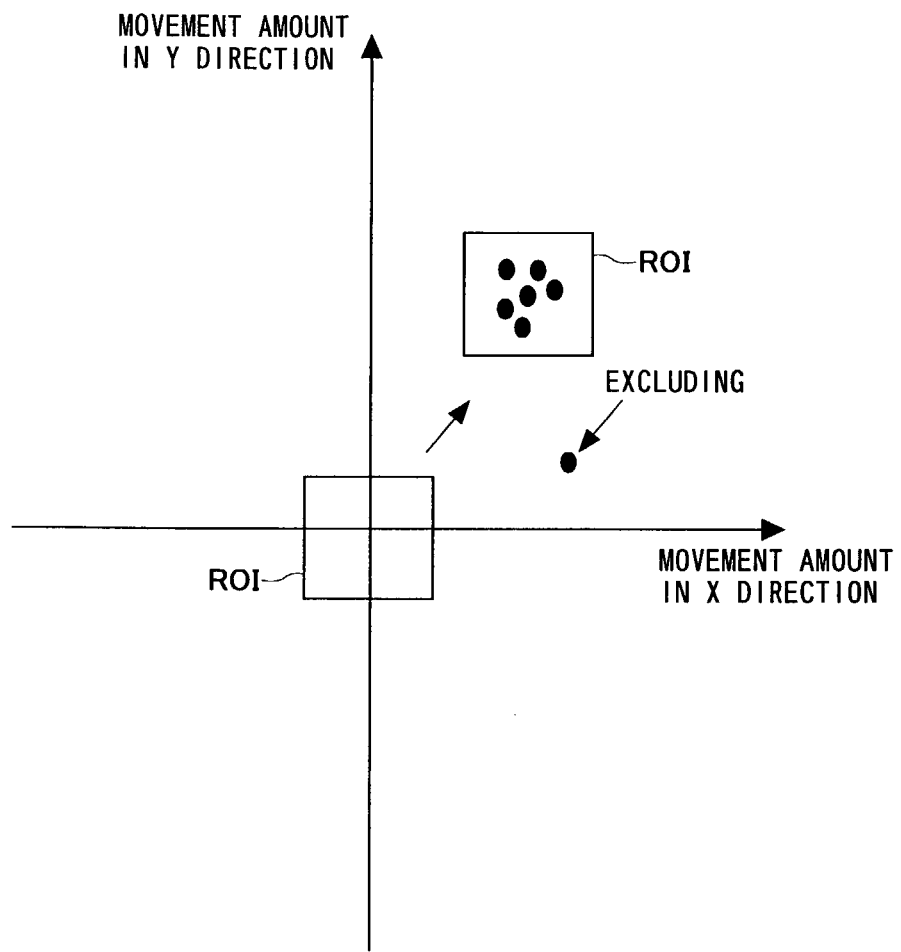
FIG. 5 is an explanatory diagram conceptually describing processing for extracting data from a plurality of characterizing points with the ultrasonic diagnosis apparatus.

Instead of calculation by the representative value calculation means 46a as described above, other-various-computation processing 46b may perform calculation. For example, as shown in FIG. 5, an arrangement may be preferably made wherein the movement amount distribution (statistical distribution) detected at a plurality of characterizing points neighboring each other is used, and exclusion processing for excluding characterizing points situated far from the distribution. Thus, reliability can be improved.

For example, provided that only one characterizing point obtains a different tracking result from those of other characterizing points due to noise or the like, by ordinary processing, the calculated average contains the tracking result of the particular characterizing point. On the contrary, with statistical distribution as shown in FIG. 5, the average excluding the above characterizing point is calculated, using dedicated program for exclusion processing. Thus, characterizing points with poor precision are excluded, thereby calculated results with higher precision may be obtained.

Note that the statistical distribution is preferably a distribution based upon variance and standard deviation. In such a distribution, in the event that only one characterizing point is situated outside the reliable range, for example, processing wherein the above point is excluded is performed.

Thus, processing for excluding tracking points situated externally from the reliable range in the statistical distribution is performed for tracking points situated closely one to another within a certain area, thereby enabling calculation precision of a representative value, average, or the like, of the characterizing points to be improved.

In addition, an arrangement may be made wherein the other-various-computation processing 46b performs grid pitch adjusting processing (means) for automatically adjusting (virtual) grid pitch so that at least N number of characterizing points are contained in one grid. Note that the greater the grid pitch is, the greater the number of the characterizing points contained in one grid is, thereby improving the stability, but leading to reduction of the spatial-resolution for measurement. Providing that required spatial-resolution is different for the X direction and the Y direction, a (virtual) grid with two pitches different in the X direction and the Y direction is formed so as to increase the number of the characterizing points contained in one grid, thereby enabling tracing of the characterizing points to be reliably performed without reduction of the required spatial-resolution.

Provided that the spatial-resolution of the ultrasonic diagnosis apparatus is known, the spacing of the region of interest in a grid pattern, i.e., the suitable range of pitch of the grid pattern can be determined. For example, the thickness of cardiac muscle is approximately 10 mm to 15 mm, and there is the need to contain a plurality of grid units within the region of the cardiac muscle. In this case, reducing the pitch of grid so as to improve the spatial-resolution prevents one grid from containing a number of characterizing points. On the other hand, extending the grid pitch makes the spatial-resolution reduced. Accordingly, the grid pitch is preferably around 5 mm, which is the size wherein the spatial-resolution thereof is acceptable and one grid can contain a plurality of characterizing points. Note that in the event that there are no characterizing points in one grid unit, an arrangement may be made wherein notice that there are no characterizing points within the grid unit is displayed.

With this arrangement, the greater the number of characterizing points in one grid is, the greater the precision of the representative value obtained from the tracking results of the characterizing points is, and accordingly, an arrangement may be made wherein marks indicating reliability of precision are displayed with different colors, for example, in proportion to the number of characterizing points contained within one grid.

Note that the present invention is not restricted to tracking methods as described above by way of the examples, but rather, any tracking method can be employed.

The second region-of-interest setting unit 42c moves each grid point of the region of interest based upon the movement information with regard to the tracked a plurality of characterizing points. Thus, the region of interest is deformed on the image. At this time, in the event that the other-various-computation processing 46b performs processing such as correction or the like, for the tracking results of the characterizing points using the statistical distribution or the like, the position of the region of interest (each grid point) is changed and subjected to processing based upon the movement information with regard to the characterizing points subjected to correction.

The second region-of-interest setting unit 42c is preferably made up of correction means for correcting the position of the region of interest based upon the statistical distribution of a plurality of characterizing points within the region of interest. Thus, correction processing can be performed for the position of the region of interest based upon the statistical distribution.

The physical parameter calculation means 47 has functions for calculating specific physical parameters (displacement, velocity, acceleration, distortion, etc.) based upon information with regard to the characterizing points contained in each region of interest, or representative value of the tracking results. Similarly, the physical parameter calculation means 47 calculates physical parameters based upon the deformation of the region of interest, and the movement information with regard to the region of interest. Using the tracking method described above, the temporal change in the position of each characterizing point (which is denoted by "TP" in FIGS. 6(a) and 6(b) or each grid point (which is denoted by "KP" in FIGS. 6(a) and 6(b) can be measured.

The physical parameters which are important in the clinical field are then calculated from the tracking results of these grid points. With the present embodiment, detailed description will be made regarding the displacement, velocity, acceleration, distortion, contraction-beginning time phase, or the like, in the case of analysis of the heart as an example.

With setting the analysis beginning time phase at an end-diastole, the displacement is obtained by calculating the (two-dimensional or three-dimensional) distance of the change in the position of the grid point from the position of the grid point at the analysis beginning time phase. In general, it is known that the greater the displacement is, the better the contractility is.

The velocity is calculated by taking the first differential of the above-described displacement as a movement velocity of the tissue corresponding to the grid point. The velocity may be calculated as a vector property (amplitude and direction), or may be defined as a scalar property (differential regarding the amplitude of the displacement). In general, it is known that contraction velocity or expansion velocity, the ratio of the blood-flow velocity thereto, or the like, reflect the cardiac performance.

The acceleration is calculated by taking the second differential of the above-described displacement as the movement acceleration of the tissue corresponding to the grid point. The user obtains a mark indicating the timing of beginning of systole or diastole by displaying the acceleration of each grid point.

Considering the one-dimensional distortion which is the simplest example, the one-dimensional distortion is defined $(L(t)-L_O)/L_O$ (dimensionless), where $L_O$ is initial value of the grid spacing (or spacing of characterizing points) and L(t) is the grid spacing at the time point (t). The distortion has a different value depending upon the contraction or expansion, and is represented in percentages.

Concerning two-dimensional distortion or three-dimensional distortion, the distortion can be separated into the distortion component made up of the expansion/contraction distortion and the displacement distortion, and the rotation component by separating the deformation tensor $D_{ij}$ into the symmetric tensor $E_{ij}$ and asymmetric tensor $F_{ij}$.

In particular, both the change in the wall thickness and the expansion/contraction in the longitudinal direction of cardiac muscle, which are important in the clinical field, can be evaluated at the same time by taking the coordinate axes in the directions along the endocardium and orthogonal thereto. Thus, the directional dependence of the analysis, which is a serious problem with conventional arrangements, can be excluded.

The automatic contour extraction technique is preferably applied to the present embodiment for setting the coordinate system along the endocardium of the heart in a simple manner. Thus, the endocardium can be automatically extracted at each time phase, and the distortion component along or orthogonal to the direction can be calculated from the deformation tensor obtained from the grid points. While an arrangement may be made wherein one-dimensional distortion is obtained for simplification, in this case, the rotation component cannot be separated.

With ultrasonic diagnosis, in many cases, a medical doctor uses the properties of tissue deformation such as the distortion of tissue, distortion velocity, and so forth, for measurement. For example, the distortion with regard to the muscular tissue is in proportion to the ratio of the change in the length of the muscular tissue during a predetermined time period, to the initial length of the muscular tissue. An arrangement may be made wherein the rate of the change in the distortion (distortion rate, distortion velocity, etc.) is visually displayed as a computer color-enhanced image corresponding to various distortion velocities.

The distortion velocity provides a direct and quantitative scale for the contractility and expansibility of the cardiac muscle. The local distortion velocity component along the longitudinal axis of the heart can be measured by taking images along the cardiac muscle. Furthermore, information regarding the local contraction and expansion of the cardiac wall can be obtained by measuring the distortion velocity component. The distortion velocity component orthogonal to the cardiac wall can also be obtained by taking images with parasternal imaging. Information with regard to the hypertrophy of local muscle can be obtained by obtaining the distortion velocity component orthogonal to the cardiac wall. As described above, the distortion velocity image can help the medical doctor with several diagnosis of the heart, which is the latent advantages.

Moreover, the change in the velocity of the cardiac muscle can be used for diagnosis of the rejection after the heart transplantation, diagnosis of the state of activation of the mechanical movement within the heart chamber or the like, for example, and other physical parameters can be used for measurement of the hypertrophy of the cardiac wall, position determination for the abnormal transmission paths from the atrium to the ventricle (information with regard to the depth of the path within the cardiac muscle for determining which of the catheterization or surgery is employed for the patient), or the like.

The various processing 48 preferably performs fitting processing in space-time, interpolation processing, or filtering processing, for various physical parameters calculated by the above-described physical parameter calculation means 47. Thus, influence of noise or the like can be excluded with regard to the physical parameters.

In particular, concerning periodical movement of the cardiac muscle or the like, data without influence of noise can be obtained by sampling only the components with frequencies up to a certain maximal frequency, using the Fourier fitting in the time direction. An arrangement may be made wherein moving average using time information, filtering with a low-pass filter, smoothing processing, or the like is performed for reducing noise. Thus, the precision can be improved using time information.

The display processing means 49 performs display processing (display control) for displaying the various physical parameters calculated by the above-described physical parameter calculation means 47, on the display unit.

In this regard, an arrangement may be made wherein the averages for sixteen divisions corresponding to the ASE (American Society of Echocardiography) wall movement evaluation, or the like, are displayed. Similarly, an arrangement may be made wherein the region for calculation is separated into the endocardium portion and the epicardium portion, and calculation is performed for the separated portions, respectively, for obtaining the difference of the physical parameters between the endocardium and the epicardium, which is known to be important in the clinical field. It is known that contraction/expansion movement of the endocardium is generally greater than that of the epicardium. However, in the event that the movement of the endocardium potion is reduced due to ischemia, the movement of the epicardium increases in compensation for the endocardium. An arrangement may be made wherein these physical parameters are subjected to color-coding and are superimposed on the image for displaying, thereby enabling the state of the cardiac performance capability to be intuitively recognized.

Figure 7:
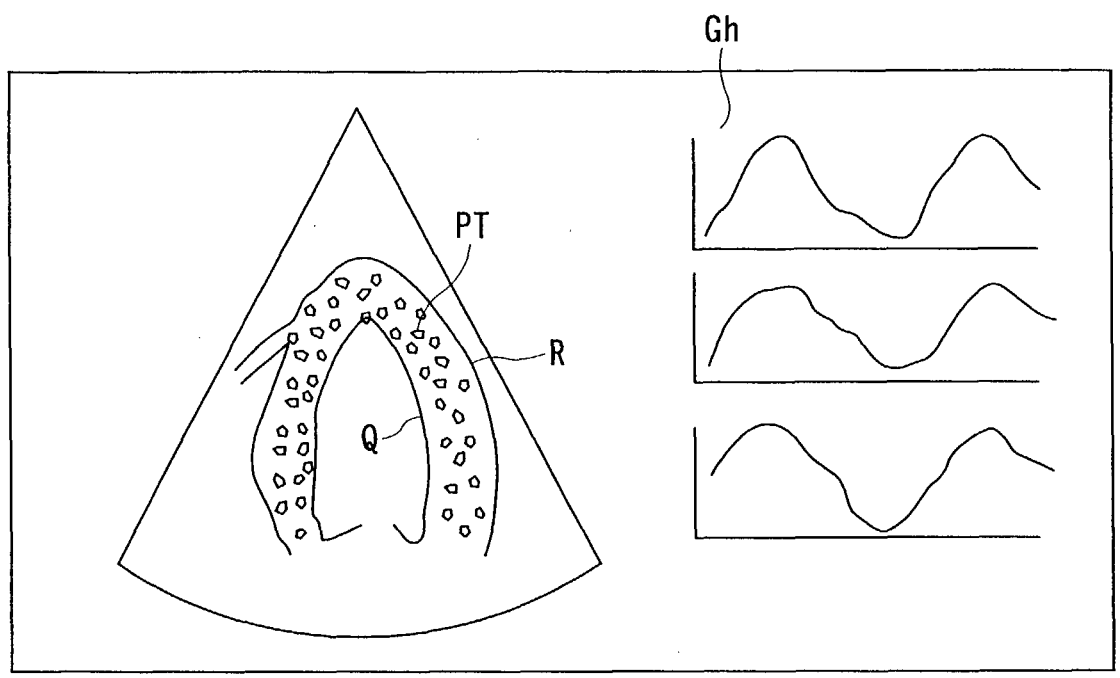
FIG. 7 is an explanatory diagram describing an example of displaying state displayed on the display unit of the ultrasonic diagnosis apparatus.

FIG. 7 is an explanatory diagram illustrating an example wherein the calculated results of the physical parameters after tracking are displayed. Upon the user operating the operation input unit 3, a predetermined screen is activated, and the calculated results are displayed on the display unit 14.

With the example shown in FIG. 7, a plurality of characterizing points TP are displayed on an ultrasonic image wherein the myocardial region surrounded by the endocardium Q and the epicardium R are displayed. In this case, the region of interest has been set to the myocardial region beforehand, so the characterizing points situated outside the myocardial region are not calculated or displayed, for example.

The physical parameters include the displacement, velocity, acceleration, distortion, and the like, for examples. The physical parameters which are to be referred, e.g., the change in the distortion as time elapsing, or the like are displayed in a format as indicated with charts Gh. That is to say, in the event that the physical parameters are calculated for temporally continuous animated images, the change in the physical parameters can be indicated with chart displaying the calculation results, which is useful for understanding the temporal change in the physical parameters. The calculated results of the physical parameters are stored in a recording medium 32, for example.

The user can preferably perform addition or cancel of various displaying items (including parameters) without restriction. Only the specified physical parameter items are displayed, so the amount of information can be adjusted as appropriate, thereby enabling a screen configuration comprehensible for users to be provided.

(Procedures for Processing)

Description will be made below regarding actions of the software configuration as described above, of the ultrasonic diagnosis apparatus according to the present embodiment.

The time phase-of-interest setting means 42*a* sets a time phase of interest on the ultrasonic image acquired by the ultrasonic image acquisition means 41*a*. Furthermore, upon the region of interest being set by the first region-of-interest setting unit 42*b* and the second region-of-interest setting unit 42*c*, (or by automatic contour extraction processing), the image processing means 41*b* performs processing for specifying the portion corresponding to the region of interest on the ultrasonic image.

An arrangement may be made wherein the time phase-of-interest setting means 42*a*, the first region-of-interest setting means 42*b*, and the second region-of-interest setting means 42*c*, do not perform setting processing, and in the event that the processing is not performed, ultrasonic images are output from the image processing means 41*b*.

The pre-processing means 43 performs pre-processing (dynamic range compression processing, binary processing, etc.) for the ultrasonic images so that the following tracking is reliably performed with good precision for various types of the ultrasonic images.

Subsequently, the characterizing extraction means 44 extracts a plurality of specific characterizing points which can be temporally tracked (i.e., the points wherein tracking can be performed without failure) on the ultrasonic image using the corner detection or the like. It is needless to say that in the event that the first region-of-interest setting means 42*b* has set the region of interest ROI1 for tracking, extraction processing for a plurality of characterizing points is performed in only the range of the region of interest ROI1 for tracking, which has been set.

The characterizing points extracted as described above are subjected to display processing by the display processing means 49, to be visualized on the ultrasonic image. For example, the characterizing points are indicated with color-enhanced dots, or the like, and are synthesized with the ultrasonic image (see FIG. 3(*a*)). Provided that the region of interest in a grid pattern is specified, the state will be as shown in FIG. 4(*a*). An arrangement may be also made wherein the characterizing points are not displayed, and only the region of interest in a grid pattern is displayed, which further facilitates observation.

Subsequently, upon instructions being made for tracking in the event of displaying the trackable characterizing points, the characterizing point tracking means 45 performs temporal tracking processing for the extracted characterizing points.

Subsequently, in the event of calculating a representative value for a plurality of characterizing points, for example, the representative value calculation means 46*a* calculates a representative value.

On the other hand, in the event that various types of processing such as correction processing for excluding specific characterizing points outside the reliable range of the statistical distribution is performed for the tracking results, processing for automatically adjusting grid pitch, or the like, the other-various-computation processing 46*b* performs various types of processing.

The second region-of-interest setting unit 42*c* changes and moves each grid point KP of the region of interest ROI2 based upon the movement information with regard to the tracked characterizing points which have been correlated with grid points beforehand, and as a result, the shape of the region of interest ROI2 is deformed.

Furthermore, the physical parameter calculation means 47 calculates various types of physical parameters, e.g., distortion or the like, based upon the tracking results subjected to the processing described above, i.e., the deformation amount of the region of interest, the movement amount of the grid points, or the like.

These calculated results are subjected to filtering processing or the like by the various processing 48, and subsequently, are subjected to color-coding or the like, by the display processing means 49 if necessary, and are then subjected to display processing so as to be displayed on the display unit. (see FIG. 7)

As described above, temporally trackable characterizing points are automatically extracted on an ultrasonic image by the characterizing point extraction means. Thus, the trackable characterizing points which can be tracked can be easily extracted. Tracking is performed for the extracted characterizing points, and various physical parameters are calculated based thereupon, thereby reducing the time period for calculation.

That is to say, all the points cannot be tracked on the ultrasonic image, so portions which can be readily tracked, e.g., all the trackable characterizing points in the peripheral region including the cardiac muscle proper, for example, are automatically displayed on the screen at the same time. Accordingly, there is no need for the user manually to operate several points within the cardiac muscle for confirmation point-by-point as with conventional arrangements, but rather a plurality of trackable points can be extracted in the entire myocardial region at the same time, thereby reducing the burden placed onto the user.

Furthermore, movement amount of an arbitrary portion (e.g., grid point) is estimated from the tracking results of the plurality of characterizing points. That is to say, while the characterizing points are situated and displayed with irregular pitch at random, the grid points of the grid pattern with regular pitch are correlated with the characterizing points, thereby enabling the precision to be improved.

Moreover, a representative value for the tracking results of the plurality of characterizing points is correlated with a grid point in the case of correlating with a grid point. Thus, in addition to interpolation processing wherein the data with irregular pitch is corrected into the data with regular pitch, the representative value is correlated with the distortion, velocity, or the like, at the local portion, thereby enabling the precision to be improved.

Conventionally, calculation for the distortion employs the tissue Doppler method, wherein the difference of velocities of two points, i.e., $(V_2-V_1)$ is calculated, and the distance is calculated by time-integrating the calculated differences. That is, the distance obtained from the velocity detected by Doppler method is a extremely small phase difference, i.e., a phase difference less than the ultrasonic wavelength (e.g., 1 mm or less) and a value far less than the movement of the heart to be obtained. So there is the need to integrate the velocity over time for obtaining the macroscopic movement, leading to accumulated error margin. Furthermore, with the Doppler method, an assumption is made with regard to the movement in a different direction (the direction which is not parallel with the beam direction) with the projection component in the normal direction, or the like, based upon the velocity in the direction of the ultrasonic beam, angular correction is performed to calculate the original movement, and consequently, assumption of the movement direction has been necessary. Moreover, with the Doppler methods, while various methods using two-dimensional cross-correlation have been proposed, there is the difficulty in that tracking cannot be readily made in other directions as described above (in particular, the direction wherein an angle formed between the beam direction and the correction direction for velocity greater than a predetermined angle near 90°).

On the contrary, with the present embodiment, processing is performed based upon an image, not phase difference, and accordingly, tracking can be made even if moving in a different direction as described above (e.g., direction orthogonal to the beam direction), and thus, there is the advantage of tracking, thereby improving the precision, and thus, the risk of incorrect diagnosis due to the portions which might contain large margin of error, can be avoided.

As described above, tracking can be easily and accurately performed for the characterizing points contained within an arbitrary region of interest, which has been set. The present embodiment can perform calculation and displaying processing for the physical parameters such as the Lagrange distortion or the like, with high time-resolution and low costs, as compared with MRI systems. Also, with the present embodiment, the same processing can be performed with low costs and good precision without requiring a large-scale circuit, integration processing, or the like, as compared with Doppler methods.

In particular, concerning the heart region, the information with regard to the specific directions according to the shape of the heart (contraction, expansion, etc.) can be analyzed, thereby enabling the cardiac performance to be easily and objectively evaluated with good precision. Furthermore, the characterizing points within the cardiac muscle can be tracked, and the physical parameters such as the distortion are quantitatively evaluated, thereby making a contribution to diagnosis.

Moreover, tracking is performed for only the characterizing points within the predetermined region of interest, thereby reducing the time period for calculation.

Moreover, the region of interest is set in a grid pattern on the image of organism as described above, and the movement amount at an arbitrary position (of grit points) is estimated from the tracking results of the characterizing points, so that the characterizing point data with irregular pitch is correlated with the grid points, thereby facilitating computation for the distortion or the like, and enabling intuitive recognition. Therefore, the region of interest is preferably made up of grid points of a grid pattern with regular pitch (information obtained from characterizing points with irregular pitch is subjected to interpolation, and is converted into the information with regular pitch). Thus, the grid points of a grid pattern with regular pitch facilitate computation, and enables intuitive recognition.

Moreover, a representative value is calculated from the tracking results of the plurality of characterizing points (calculating an average, or extracting only points with high reliability), thereby improving stability. Furthermore, tracking results are calculated from the statistical distribution of the movement information with regard to the plurality of characterizing points within the region of interest or the portions spatially neighboring each other, thereby improving precision. In addition, calculation of the results is performed for fitting, interpolation, or filtering, in the time axis direction, thereby improving precision, and enabling specific components to be extracted.

Moreover, representative values (averages or the like) of the tracking results or the physical parameters are preferably calculated and displayed for predetermined regions. Thus, the stability of the results can be improved.

Furthermore, the deformation tensor is separated into a symmetric. portion and an asymmetric portion, and a configuration made up of the rotation component and the distortion component is formed, and thus, the two-dimensional and three-dimensional distortions can be grasped as well as the one-dimensional distortion, thereby enabling the contractility and the expansibility to be accurately evaluated.

With the physical parameters, the direction of the main axis thereof is preferably to be the direction normal or tangential to the extracted Endocardium face or Epicardium face. Thus, the influence of the shortening and thickening of the cardiac muscle can be separated.

(Second Embodiment)

Next, a second embodiment according to the present invention will be described with reference to FIG. 8. While, in the first embodiment described above, the determined region of interest is made up of a grid pattern as shown in FIG. 4(*a*), but rather, the present invention is not restricted thereto, and an arrangement may be made wherein the region configuration is made up of six segments for evaluating the wall movement, for example, which is stipulated by the ASE, or the like.

Figure 8:
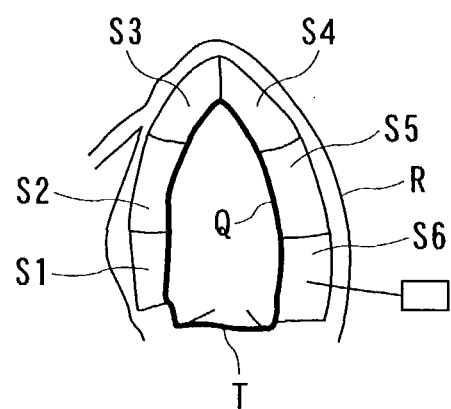
FIG. 8 is an explanatory diagram describing an example of a region of interest of six segments.

Specifically, as shown in FIG. 8, the present embodiment has a configuration made up of six divided regions (segments), S1 through S6, so that the displacement or the like of each segment can be recognized. At this time, the user judges the amplitude of the wall movement by observation, and performs scoring (1, 2, 3, 4, 5) for the wall movement, such as "normal", "decline of movement", or the like, by clicking a mouse. Moreover, the present embodiment has a configuration wherein the information with regard to the degree of the distortion, movement, or the like, for each segment region, can be automatically displayed with different colors, thereby improving utility. It is needless to say that the method may be applied to an arrangement wherein the region of interest is made up of a grid pattern.

As the display method for contour information, for example, the contour line T may be displayed with a bold line or a different color as compared with different contour lines, as shown in FIG. 8. In this way, the user can easily and visually recognize the contour portions.

As for displaying for divided portions corresponding to the image, as shown in FIG. 8, for example, the cardiac wall is displayed, the divided portion from the right annulus portion to the apex portion and the divided portion from the left annulus portion to the apex portion are further classified into three portions, respectively, inside the cardiac wall. The contour line (cardiac wall contour) is classified with different colors corresponding to the classified portions S1, S2, S3, S4, S5, S6, and are superimposed on the tomographic image of the heart to be displayed.

The above-described classification into three portions is preferably to be a classification useful for diagnosis, for example, a classification wherein the portion is classified into the base portion, middle portion, and apex portion. Thus, the cardiac wall is specified, and the contour line thereof is displayed with different color corresponding to each specified portion, and thus the user can suitably classify the cardiac wall, and can easily and visually recognize the positions of the cardiac wall region on the image.

Detailed description of displayed components will be made below. Description will be made regarding a case wherein the region from the left annulus portion to the apex portion, and the region from the apex portion to the right annulus, are classified into three regions, respectively, as an example.

First of all, a plurality of divided portions are specified on the cardiac wall contour. Then, the cardiac wall is classified with a required segment unit by using the plurality of dividing points. For example, the region from the left annulus portion to the apex portion, and the region from the apex portion to the right annulus portion, are classified into three regions, i.e., the base portion, middle portion, apex portion, respectively.

Upon the user performing predetermined operations using the operation input unit 3 such as a trackball or the like, on the longitudinal tomographic image of the left ventricle, the contour of the cardiac muscle, e.g., the portion corresponding to the endocardium Q, is automatically extracted, and is enhanced and displayed as a contour line T for tracing. The myocardial contour tracing automatically extracts the boundary between the heart chamber and the cardiac muscle based upon the luminance gradient using various methods. The region specified by the tracing is taken as a region of interest.

In the event of tracking the endocardium T, or the like, the region of interest is moved and deformed following the movement of the endocardium T. Subsequently, the physical parameters are calculated based upon the information with regard to the characterizing points within the region of interest which has been moved and deformed, and the region of interest is color-enhanced based upon the physical parameters.

In the event that the region of interest is divided as shown in FIG. 8, and one divided region has a portion which cannot be tracked, the physical parameters are calculated for the divided region from the characterizing points in the range excluding the portion.

As described above, for example, the tomographic images of the heart of the subject are time-sequentially obtained from the ultrasonic diagnosis apparatus, the heart contour extraction is performed for the images, and the extracted contour images are stored in the image memory 22 as cardiac wall contour information. For example, for the cardiac wall contour, points on the contour, such as points of the apex portion and points of the annulus portion, are automatically detected by a detection unit (not shown in the drawing) based upon the cardiac wall contour information using the information with regard to the shape of the cardiac wall contour, the curvature of the contour, and the like. The cardiac wall contour is divided by the contour dividing unit based upon the positions of the detected points. The divided cardiac wall contour is classified into regions useful for diagnosis, and the regions are displayed with at least one of value displaying, chart displaying, and color-enhanced displaying of the cardiac wall. The contour information or divided portion information can be stored in the image memory.

Since the apex portion and the annulus portion have clear shape features, using the detailed points thereof as characterizing points enables the positions of the apex portion and annulus portion to be accurately correlated with the image. Moreover, the cardiac wall contour is divided based upon the apex portion and the annulus portion, and thus the wall can be suitably correlated with the image.

Furthermore, an arrangement may be made wherein, on the occasion of calculating the physical parameters, calculation is performed by specifying the region of interest in a grid pattern, and on the occasion of finally displaying as a user-interface, the display arrangement is configured so that the user can easily recognize, as shown in FIG. 8.

Moreover, an arrangement may be made wherein the distortion or the like at the characterizing points is subjected to interpolation, and a mark (color) is placed onto each pixel for indicating the change in the physical parameter (distortion, etc.), so as to display in a manner whereby the color is smoothly changed. Thus, various parameters can be subjected to color-coding and displayed.

One display example with color-coding is illustrated in FIGS. 9(*a*) and 9(*b*). FIG. 9(*a*) depicts tomographic image indicating the configuration of tissue is illustrated, and in FIG. 9(*b*), distortion of a cardiac muscle is overlaid on the tomographic image, but their directions (extension or contraction) are not separated yet. A color bar in FIG. 9(*b*) shows the amplitudes of the distortion of the cardiac muscle, wherein an exemplified color allocation is such that the distortion of the cardiac muscle having smaller amplitudes are depicted in light blue or similar hue thereto, while corrected velocities having larger amplitudes are depicted in dark blue or similar hue thereto.

FIGS. 10(*a*) through 10(*e*) illustrate examples of color bars that can be displayed.

Figure 9B:
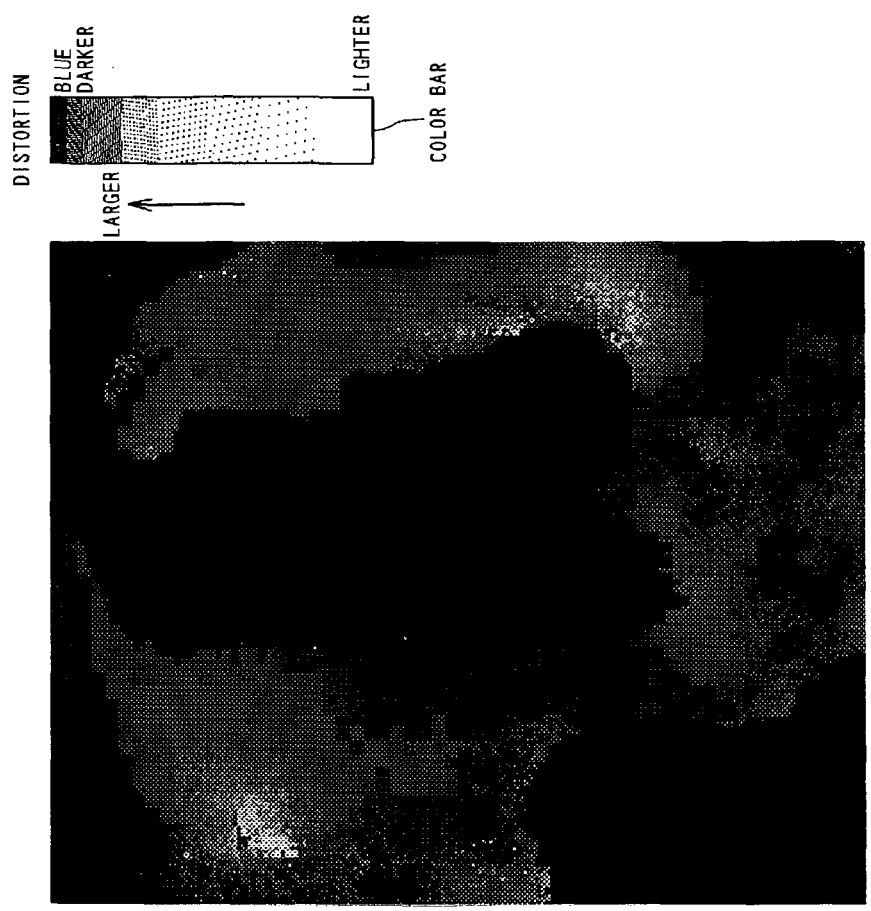
Figure 9A:
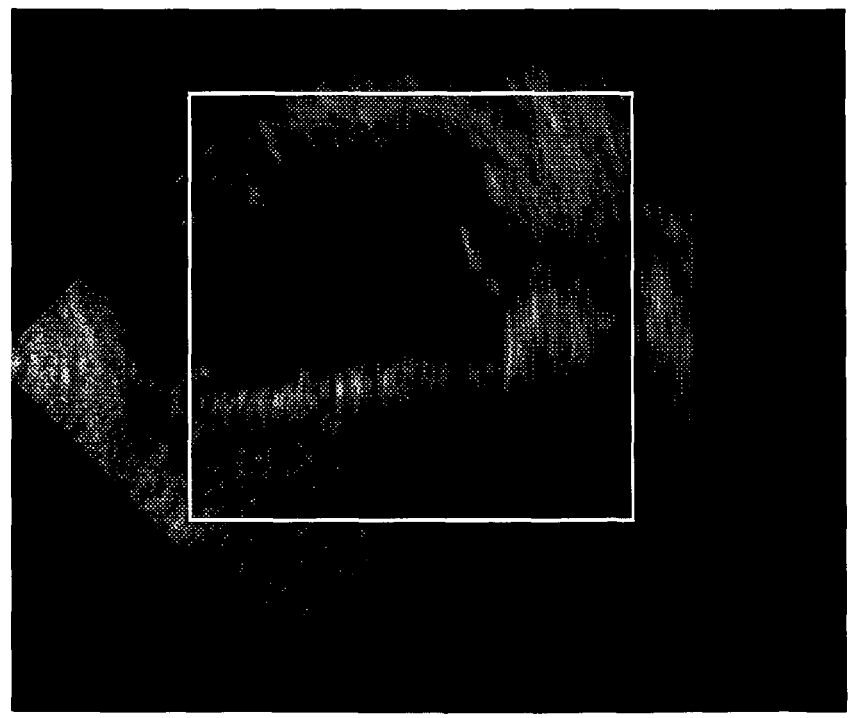
Figure 9D:
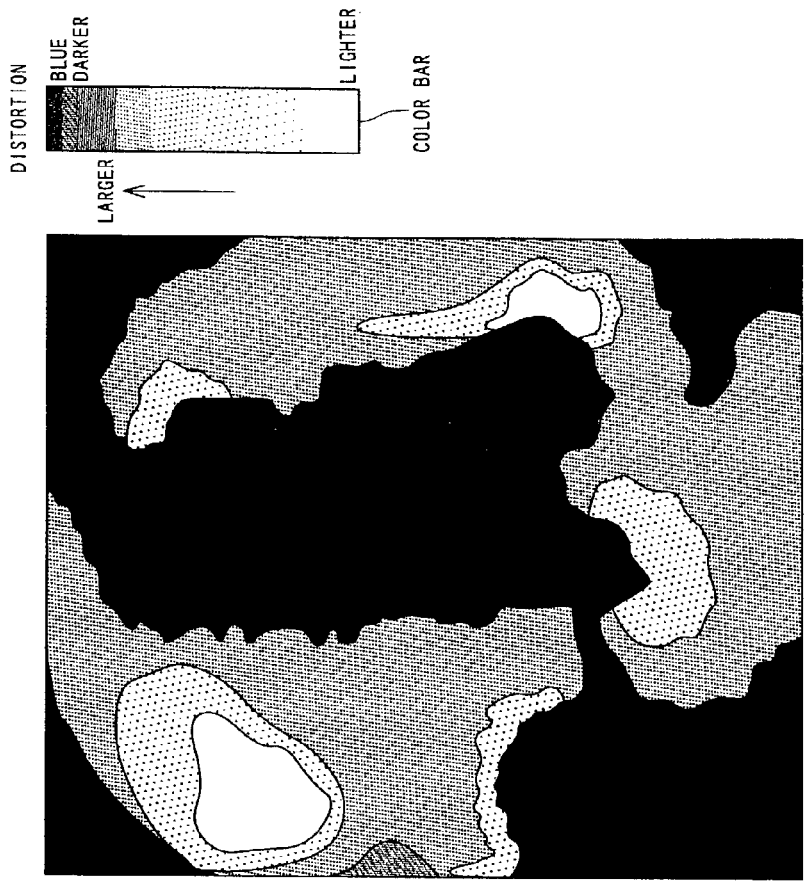
FIGS. 9(c) and 9(d) are their simplified diagrams substitutive for FIG. 9(a) and 9(b) respectively.
Figure 9C:
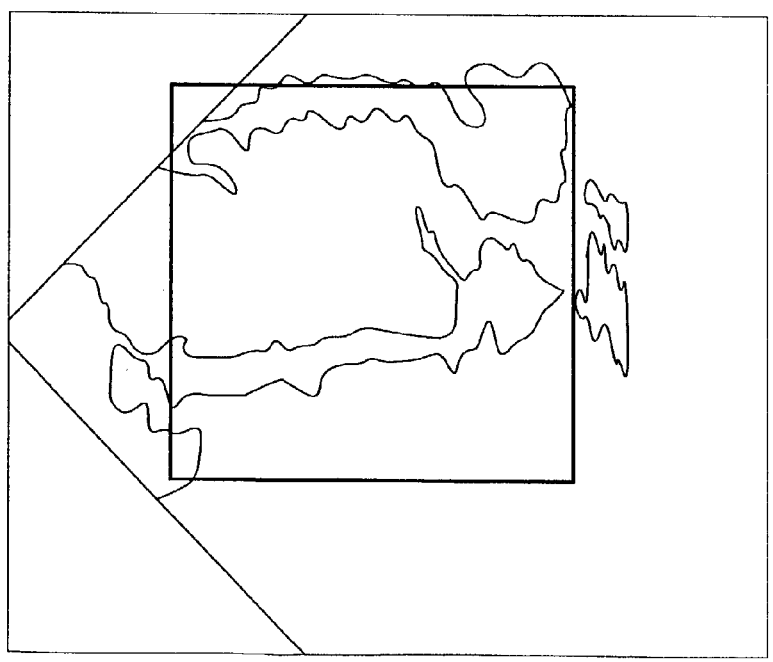

FIG. 10(a) illustrates, like the case shown in FIG. 9(b), an example of a color bar that indicates smaller distortion of the cardiac muscle in red, for example, and the hue is shifted to yellow, for example, as the distortion of the cardiac muscle increases.

FIG. 10(b) illustrates another example of display of the color bar, in which the display of distortion velocity is combined with that of the distortion shown in FIG. 10(a). In this example, the larger distortion velocity of the cardiac muscle, the brighter a hue to be used in the color bar, and vice versa. With this manner, the distortion velocity is displayed correlated with the distortion simultaneously, so that a higher visibility is given to the cardiac muscle to be displayed.

Figure 13A:
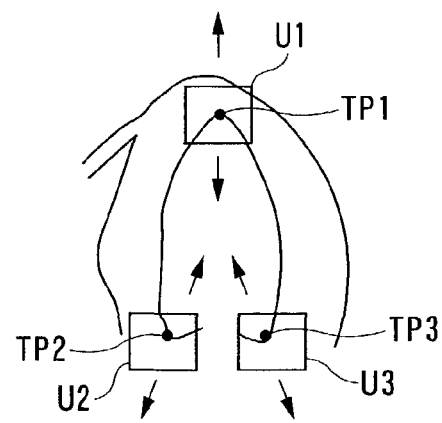

FIG. 10(c) exemplifies the display of another color bar, in which directional separation is additionally performed in the display of distortion of the cardiac muscle shown in FIG. 13(a). In this case, by way of an example, a contracting distortion of the cardiac muscle is depicted in warm hues, while a extending distortion is depicted in cold hues. This directional separation may make it possible that types of distortion of the cardiac muscle can be distinguished one from the other in an easier manner.

FIG. 10(d) also exemplifies another color bar, which is composed by combining the display of directionally separated distortion shown in FIG. 10(c) with the display of the distortion velocity. This display configuration is able to have the advantages obtained by both of the examples shown in FIG. 10(b) and 10(c).

The setting of the region of interest is automatically made using the results of automatic contour extraction (for the heart or the myocardial region). At this time, the contour extraction is preferably performed following the procedures wherein the endocardium is traced, and the myocardial region is extracted as a region between the endocardium and the epicardium side estimated as a side externally from the endocardium by a predetermined distance (e.g., 1 cm). Thus, setting of the region can be easily performed. Tracing of the epicardium is not always required. However, in the event that the region of interest is set onto the endocardium or epicardium of the cardiac muscle, the information with regard to the difference between the endocardium and the epicardium (corresponding to the cardiac muscle) can be obtained.

Also, the present embodiment has the configuration wherein the contour line of the endocardium T is extracted by the automatic contour extracting processing so as to set the region of interest, and thus, in the event of setting the region of interest, required contours regarding the tissue are automatically traced, so the user can intuitively recognize the size of the tissue or the like, and can specify only the tracking-required region based upon the information, thereby enabling evaluation of the wall to be efficiently performed.

It is needless to say that the automatic contour extraction processing may have a configuration wherein the contour lines of the region corresponding to the epicardium as well as the endocardium are automatically displayed. In this case, characterizing points are detected and extracted within the myocardial region between the endocardium and the epicardium, tracking is performed within the region, thereby enabling unnecessary processing such as characterizing point extraction processing in unnecessary portions to be avoided.

Thus, all the trackable characterizing points are not extracted within the entire heart, but rather, only the portions and regions necessary for setting the region of interest are set so as to avoid the calculation for unnecessary portions, thereby enabling calculation to be efficiently performed, reducing the burden for processing, and improving processing speed.

Concerning the automatic contour extraction processing for setting of the region of interest, it is preferable that the contours of the object are extracted by a contour extraction unit (not shown in the drawing) based upon the image information, for example. Several contour extraction methods can be applied to the contour extraction unit. For example, the methods include a method based upon the contour model defining the image energy, elastic energy, and so forth, a method for extracting closed contours following the image being subjected to binary processing, a method for extracting contours by connecting contour candidate points on rasters extending in a radial pattern from a center point which the user input, and the like. The coordinate information with regard to the contours extracted as described above is stored in the recording medium 32.

In the present embodiment, detailed description was made regarding a case wherein the region from the left annulus portion to the apex portion, and the region from the apex portion to the right annulus, are classified into three regions, respectively, as an example. However, it is needless to say that the present invention is not restricted thereto, and an arrangement may be made wherein the region configuration is made up of a plurality of segments for evaluating the wall movement.

(Third Embodiment)

Figure 11:
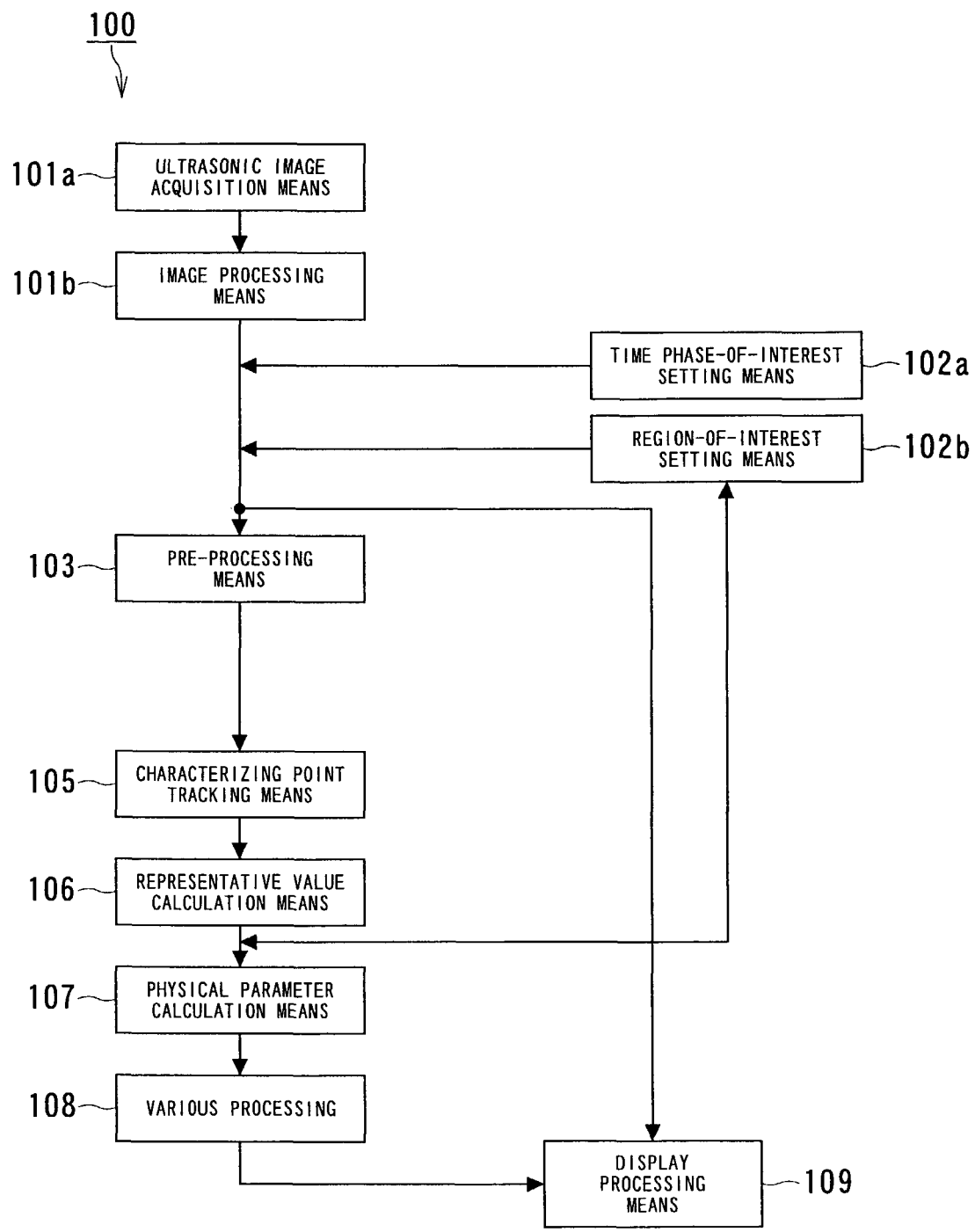
FIG. 11 is a functional block diagram illustrating an example software module configuration of an ultrasonic diagnosis apparatus according to the third embodiment of the present invention.

A third embodiment according to the present invention will be described with reference to FIGS. 11 through 13(c). Note that description will be omitted with regard to the substantially same configuration as the above-described first embodiment, and only different components will be described. FIG. 11 is a functional block diagram illustrating an example configuration of an ultrasonic diagnosis apparatus according to the present embodiment.

With the present embodiment, tracking is performed for the papillary muscle, annulus, arbitrary representative portions within the cardiac muscle, or the like, for example, and the information with regard to the macroscopic structure of the heart, for example, important in the clinical field, can be provided based upon the tracking results.

Specifically, a software module configuration 100 of the ultrasonic diagnosis apparatus according to the present embodiment comprises ultrasonic image acquisition means 101a, time phase-of-interest setting means 102a, image processing means 101b, pre-processing means 103, characterizing point tracking means 105, various processing means 108, and display processing means 109, having generally the same configuration as with the first embodiment, and region-of-interest setting means 102b for setting a plurality of regions of interest, representative value calculation means 106 for calculating a representative value for tracking results of a plurality of characterizing points within the region of interest, and physical parameter calculation means 107.

Figure 12A:
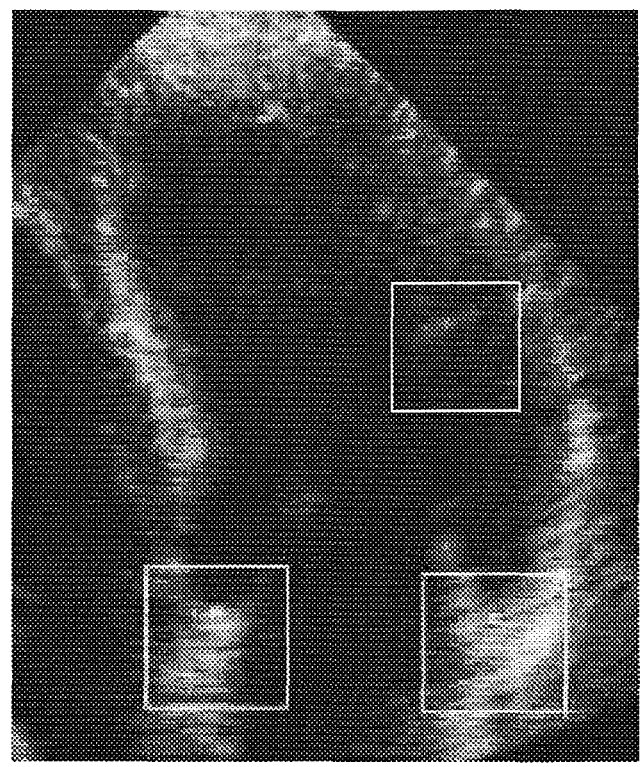
FIG. 12(a) is an explanatory diagram illustrating an example in the case of a plurality of regions of interest being specified with the ultrasonic diagnosis apparatus shown in FIG. 11.
Figure 12B:
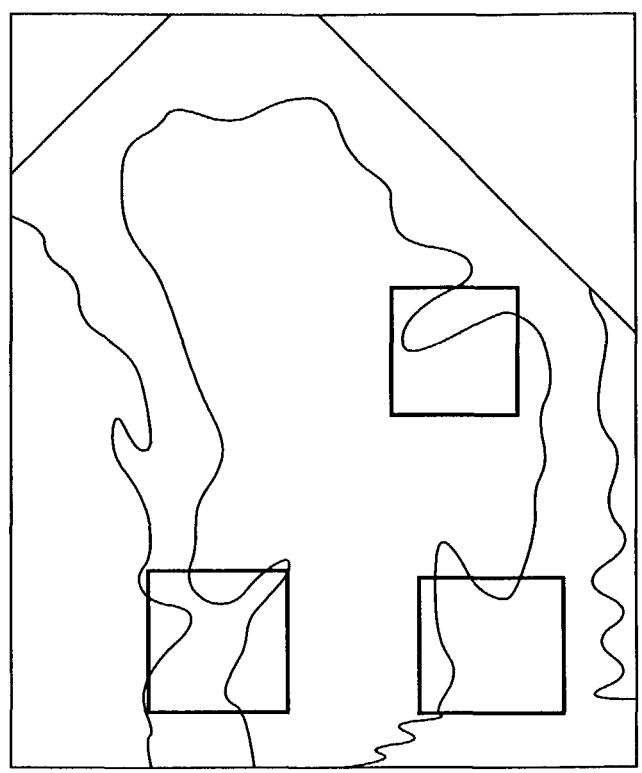
FIG. 12(b) is its simplified diagram substitutive for FIG. 12(a)

The region-of-interest setting means 102b is configured so as to be able to set a plurality of regions of interest. FIG. 12(a) indicates a scene of the regions of interest being set onto the papillary muscle and the mitral valve annulus portion. Here, the user can set the region of interest with a predetermined size onto an arbitrary point.

The representative calculation means 106 calculates a representative value from the tracking results of a plurality of characterizing points contained in the region of interest. As described above, with conventional pattern matching techniques, temporal tracking over time cannot be readily performed for portions other than characteristic structures.

Accordingly, as with the first embodiment, according to the present embodiment, a plurality of characterizing points contained in the region of interest with a predetermined large size are tracked, and calculation is performed for the representative value thereof, thereby enabling the structure within the region of interest to be precisely tracked.

The physical parameter calculation means 107 calculates specific physical parameters (displacement, velocity, acceleration, distortion, etc.) based upon the representative values of the tracking results. With mitral valve regurgitation, it is known that asytstole of the papillary muscle causes the change in the relative position relationship between the papillary muscle and the annulus portion, leading to occurrence of regurgitation.

According to the present embodiment, the user can easily obtain the relative position relationship between these points, i.e., the temporal change in various information such as the distance between the papillary muscle and the annulus, the angle enclosed by the lines connecting the papillary muscle and the annulus, or the like. With conventional arrangements, in a case of obtaining such information, there is the need for measurement to be manually performed for each time phase, which is troublesome.

The display processing unit 109 displays calculated results. An arrangement may be made wherein the information obtained from the plurality of regions of interest is displayed with charts or the change in geometrical pattern.

With the above-described configuration, first of all, the region-of-interest setting means 102b sets a plurality of regions of interest. Subsequently, the characterizing point tracking means 105 tracks characterizing points within each region of interest.

The physical parameter calculation means 107 calculates the distance between the regions of interest, the angle formed by lines connecting the regions of interest, or the like, and displays the calculated results via the display processing means 109.

While with the above-described first embodiment, a scene of the local portions being deformed is displayed, the present embodiment has no information with regard to contraction of the cardiac muscle etc., and tagging or the like, but rather displays how the configuration of the heart made up of large regions which are landmarks (regions serving as marks) such as the annulus of the left chamber, papillary muscle, apex cordis, or the like, is changed.

For example, in the case of observing the change in the size of the valve, for observing how the valve expands or narrows for each cycle following the movement of the heart, with conventional arrangement, there is the need that the user manually observes images frame-by-frame, which is extremely troublesome.

On the contrary, with the present embodiment, a plurality of regions of interest are specified so that the distance between the regions of interest, for example, the distance of the movement of the annulus, the moving distance between moving two points, can be tracked.

For example, as a concrete example wherein regions of interest are specified, Assuming that a plurality of regions of interest U1, U2, and U3, are specified, centered on three points, i.e., the apex TP1, left annulus TP2, and right annulus TP3, as shown in FIG. 13(a), following the contraction and expansion of the heart, the apex TP1, left annulus TP2, and right annulus TP3, and the FIG, U1, U2, and U3 also perform contraction and expansion, synchronously therewith.

Figure 13B:
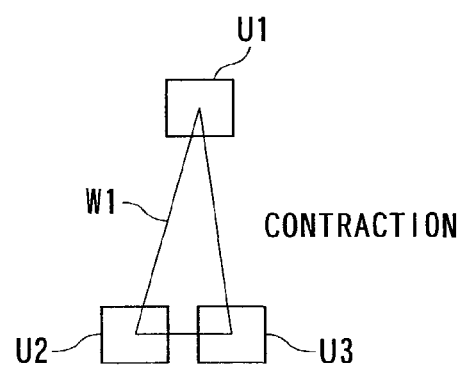

Specifically, at a systole, the distances between regions of interest, U1, U2, and U3, are narrowed, and thus, a geometric shape in a general triangle W1 is formed by lines connecting the regions of interest U1, U2, and U3, are connected as shown in FIG. 13(b).

Figure 13C:
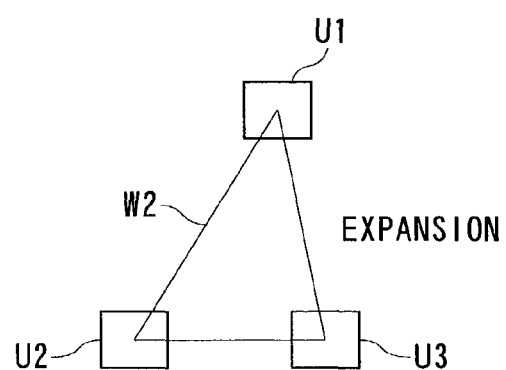

On the other hand, at a diastole, the distances between regions of interest, U1, U2, and U3, are extended, and thus, a geometric shape in a general triangle W2 (different from W1 described above) formed by lines connecting the regions of interest U1, U2, and U3 as shown in FIG. 13(c).

Under the situation as described above, the distances between the regions of interest, or angles regarding the regions of interest, are tracked in a geometric structure made up of the three points. For example, the geometric structure is a certain triangular shape in the first stage, and the shape thereof is gradually deformed into a different shape following the tracing processing, thereby enabling the degree of the contraction and the expansion of the heart to be visually recognized. With the specifying of plurality of regions of interest for tracking, the number of regions of interest is not restricted to three as with the example described above, but rather, may be two, and it is needless to say that the number of regions of interest may be greater than three (e.g., 4 or 5 points).

As described above, while the present embodiment has the same advantages as the above-described first and second embodiments, according to the present embodiment, there is the advantage of observing the change in the parameters of the macroscopic structures such as the valve, papillary muscle, apex, or the like, and the characteristic change in the shape of the heart due to myocardial infarction or the like can be accurately measured.

(Fourth Embodiment)

Figure 14:
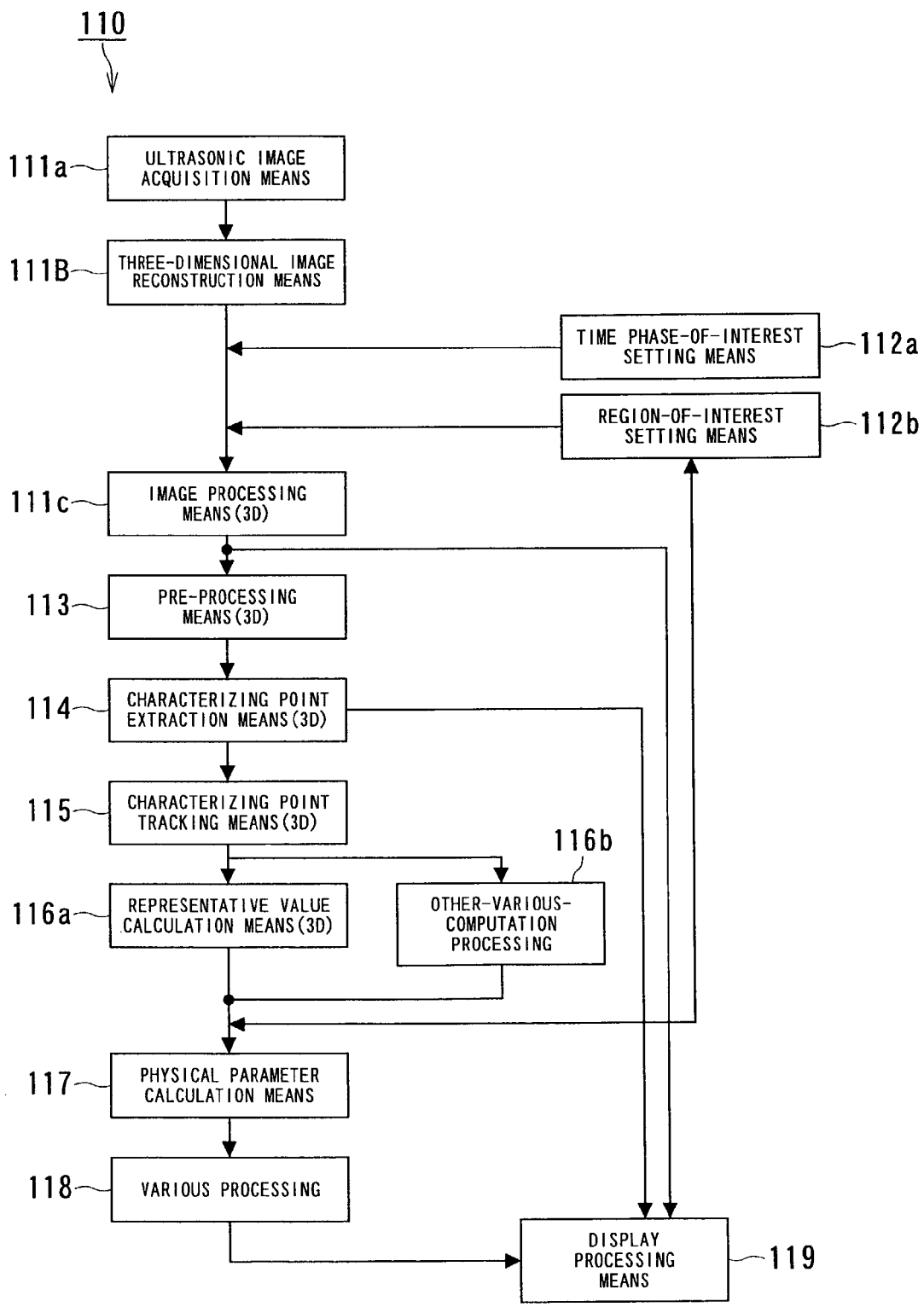
FIG. 14 is a functional block diagram illustrating an example software module configuration of an ultrasonic diagnosis apparatus according to another embodiment of the present invention.

A fourth embodiment according to the present invention will be described with reference to FIG. 14. FIG. 14 is a functional block diagram which illustrates a fourth embodiment according to the present invention.

With each embodiment as described above, detailed description has been made regarding an ultrasonic diagnosis apparatus for displaying ordinary two-dimensional images. However, in recent years, ultrasonic diagnosis apparatuses wherein three-dimensional images can be acquired in real time have been proposed. In this case, an arrangement may be made wherein a two-dimensional image is configured by taking an arbitrary cross-section from a three-dimensional image, and each embodiment described above is applied. Also, an arrangement may be made wherein the three-dimensional region of interest in a grid pattern is formed for the three-dimensional voxel data, and performs three-dimensional tracking, thereby enabling various three-dimensional physical parameters to be calculated and displayed.

Specifically, as shown in FIG. 14, a software module configuration 110 of the ultrasonic diagnosis apparatus, capable of three-dimensional displaying according to the present embodiment comprises ultrasonic image acquisition means 111a, three-dimensional image reconstruction means 111b, time phase-of-interest setting means 112a, region-of-interest setting means 112b, image processing means (3D) 111c, pre-processing means (3D) 113, characterizing extraction means (3D) 114, characterizing tracking means (3D) 115, representative value calculation means (3D) 116a, other-various computation processing 116b, physical parameter calculation means 117, various processing 118, and display processing means 119.

With the ultrasonic diagnosis apparatus having the above-described configuration, while the basic processing is the same as with the first embodiment described above, ultrasonic images acquired from the ultrasonic image acquisition means 111a are constructed by the three-dimensional reconstruction means 111b into a three-dimensional image which can be displayed in a three-dimensional manner.

Subsequently, the region-of-interest setting means 112b sets the region of interest in a three-dimensional manner, for example, in a grid pattern with a cube unit. Next, the image processing means 111c performs predetermined processing so that the region of interest specified in a three-dimensional manner is configured on the above three-dimensional image. Subsequently, the pre-processing means 113 performs pre-processing for the three-dimensional image, and the characterizing point extraction means 114 then extracts characterizing points. The characterizing points are also displayed on the three-dimensional image so that the user can recognize the three-dimensional position relationship.

Moreover, the characterizing tracking means 115 and the representative value calculation means 116a perform processing in a manner corresponding to three-dimensional images, respectively. Subsequently, the other-various computation 116b performs computation processing, the physical parameter calculation means 117 performs calculation, and the various processing 118 and the display processing means 119 perform display processing as with the above-described first embodiment.

As described above, the present embodiment has the same advantages as with other embodiments described above. While, with arrangements employing two-dimensional processing, only the expansion and contraction within a face can be recognized, with arrangements employing three-dimensional processing, the user can recognize how a grid made up of cubes with the x, y, and z axes is deformed by means of three-dimensional information. In this case, the same processing as with the above-described first embodiment is enhanced with regard to three-dimensional processing so as to perform the processing for the three-dimensional information obtained in real time, thereby enabling three-dimensional distortion to be calculated and obtained.

Note that while description has been made regarding the apparatuses and methods according to the present invention with reference to several and specific embodiments, various modifications may be made with regard to the embodiments described in this specification without departing from the spirit and scope of the invention.

With the processing programs executed by the ultrasonic diagnosis apparatus of each embodiment described above, for example, characterizing point extraction processing, characterizing tracking processing, physical parameter calculation processing, or the like, described in FIGS. 2, 11, and 14, the processing may be performed by a computer (image processing device) having the functions of the above-described processing, such as a PC, workstation, or the like, separately from the ultrasonic diagnosis apparatus.

An arrangement may be made wherein the image processing device is built in image acquisition means (modality) such as the ultrasonic diagnosis apparatus or the like. Similarly, an arrangement may be made wherein the image processing device and the image acquisition means (modality) are separated one from another. In this case, the modality is not restricted to an ultrasonic diagnosis apparatus, but rather, the image acquisition unit may be means for inputting video signals of images, for example.

Furthermore, the above-described embodiments contain various stages, and various arrangements can be further extracted from suitable combinations of a plurality of disclosed configuration components. That is, it is needless to say that the present invention contains combinations of above-described embodiments, or combinations of one of the embodiments and one of the modifications. Similarly, an arrangement may be made wherein several configuration components are excluded from the entire configuration.

Description has been made regarding an example of the embodiments according to the present invention, and modification and/or alteration can be made in a suitable range. Each embodiment indicates an example of the present invention, and does not intend to restrict the present invention.

What is claimed is:

1. An image processing apparatus comprising:
an ultrasonic image acquiring unit configured to acquire image data including a myocardial region of a subject;
a region-of-interest setting unit configured to set a plurality of regions of interest, the plurality of regions of interest being regions of interest which periodically deform on the myocardial region included in the image data;
an extraction unit configured to extract, for each of the plurality of regions of interest, a plurality of characterizing points based on the image data;
a tracking unit configured to track a movement of the positions of the plurality of characterizing points over a plurality of time points;
a representative value calculating unit configured to calculate, for each of the plurality of regions of interest, a representative value of the plurality of characterizing points for each of the plurality of time points; and
a physical parameter calculating unit configured to calculate a specific physical parameter based on a temporal change of positional relationships between the representative values for each of the plurality of regions of interest.

2. The image processing apparatus according to claim 1, wherein the region-of-interest setting unit is configured to extract a contour of the myocardial region and to set the plurality of regions of interest on the image data based on the extracted contour.

3. The image processing apparatus according to claim 2, wherein the region-of-interest setting unit is further configured to classify the myocardial region into a plurality of segments, and to set the regions of interest on the image data based on the classification.

4. The image processing apparatus according to claim 2, wherein the region-of-interest setting unit is further configured to classify the myocardial region into three segments of a base, a middle and an apex portion from an annulus to the apex of each side, and to set the regions of interest on the image data based on the classification.

5. The image processing apparatus according to claim 1, wherein the specific physical parameter is one of displacement, distortion and distortion velocity derived from deformation of the regions of interest, each region of interest set in a grid pattern, the grid pattern including a plurality of pixels therein.

6. The image processing apparatus according to claim 1, wherein the extraction unit is configured to extract the characterizing points by detecting corner points from the image data.

7. The image processing apparatus according to claim 1, wherein the region-of-interest setting unit includes a correcting unit configured to correct positional information of the plurality of regions of interest based on a statistical distribution of the plurality of characterizing points within each of the regions of interest.

8. The image processing apparatus according to claim 1, wherein the image data is three-dimensional image data.

9. The image processing apparatus according to claim 1, wherein the representative value is obtained by extraction of reliable characterizing points from a distribution based on variance or standard deviation of the plurality of characterizing point.

10. The image processing apparatus according to claim 1, wherein the physical parameter calculating unit is configured to acquire deformation tensor from information about a deformation of the plurality regions of interest, to separate the deformation tensor into a symmetric tensor and an asymmetric tensor, and to separate distortion components from rotation components.

11. The image processing apparatus according to claim 10, wherein a main axis of the specific physical parameter is oriented to a direction orthogonal or tangential to one of an extracted endocardium face and epicardium face.

12. The image processing apparatus according to claim 1, wherein the region-of-interest setting unit is configured to set each of the plurality of regions of interest in a grid pattern on the image data, the grid pattern including a plurality of pixels therein, and the region-of-interest setting unit is configured to deform each of the regions of interest by moving grid points as corners of each of the region of interest on the basis of tracked movements of the characterizing points.

13. An image processing apparatus comprising:
   ultrasonic image acquiring means for acquiring image data including a cardiac muscle of a subject;
   region-of-interest setting means for setting a plurality of regions of interest, the plurality of regions of interest being regions of interest which periodically deform on the cardiac muscle included in the image data;
   extraction means for extracting, for each of the plurality of regions of interest, a plurality of characterizing points based on the image data;
   tracking means for tracking a movement of the positions of the plurality of characterizing points over a plurality of time points;
   representative value calculating means for calculating, for each of the plurality of regions of interest, a representative value of the plurality of characterizing points for each of the plurality of time points; and
   physical parameter calculating means for calculating a specific physical parameter based on a temporal change of positional relationships between the representative values for each of the plurality of regions of intrest.

14. The image processing apparatus according to claim 13, wherein the image data is three-dimensional image data.

15. A method of processing an image for diagnosing a subject with an ultrasonic diagnosis apparatus, comprising the steps of:
   acquiring image data including a cardiac muscle of a subject with a probe device of the ultrasonic diagnosis apparatus;
   setting, with the ultrasonic diagnosis apparatus, a plurality of regions of interest, the plurality of regions of interest being regions of interest which periodically deform on the cardiac muscle included in the image data;
   extracting, with the ultrasonic diagnosis apparatus, for each of the plurality of regions of interest, a plurality of characterizing points based on the image data;
   tracking, with the ultrasonic diagnosis apparatus, a movement of the positions of the plurality of characterizing points over a plurality of time points;
   calculating, with the ultrasonic diagnosis apparatus, for each of the plurality of regions of interest, a representative value of the plurality of characterizing points for each of the plurality of time points; and
   calculating, with the ultrasonic diagnosis apparatus, a specific physical parameter based on a temporal change of positional relationships between the representative values for each of the plurality of regions of interest.

* * * * *